United States Patent
Turner et al.

(10) Patent No.: US 10,039,926 B2
(45) Date of Patent: Aug. 7, 2018

(54) APPARATUS AND METHOD FOR CREATING SMALL FOCUS DEEP HYPERTHERMIA IN TISSUE

(71) Applicants: Paul F. Turner, Salt Lake City, UT (US); Mark Hagmann, Salt Lake City, UT (US)

(72) Inventors: Paul F. Turner, Salt Lake City, UT (US); Mark Hagmann, Salt Lake City, UT (US)

(73) Assignee: Pyrexar Medical Inc., Salt Lake City, UT (US)

( * ) Notice: Subject to any disclaimer, the term of this patent is extended or adjusted under 35 U.S.C. 154(b) by 454 days.

(21) Appl. No.: 14/706,909

(22) Filed: May 7, 2015

(65) Prior Publication Data
US 2016/0015993 A1    Jan. 21, 2016

Related U.S. Application Data

(60) Provisional application No. 61/990,036, filed on May 7, 2014.

(51) Int. Cl.
*A61N 1/40* (2006.01)
*A61N 5/02* (2006.01)

(52) U.S. Cl.
CPC .............. *A61N 1/403* (2013.01); *A61N 5/025* (2013.01); *A61N 2005/027* (2013.01)

(58) Field of Classification Search
CPC ... A61N 1/403; A61N 5/025; A61N 2005/027
See application file for complete search history.

(56) References Cited

U.S. PATENT DOCUMENTS

| | | | |
|---|---|---|---|
| 4,672,980 | A | 6/1987 | Turner |
| 5,097,844 | A | 3/1992 | Turner |
| 5,503,150 | A | 4/1996 | Evans |
| 5,540,737 | A | 7/1996 | Fenn |
| 2004/0044385 | A1 | 3/2004 | Fenn et al. |

(Continued)

OTHER PUBLICATIONS

Gellermann et al.; "Simulation of different applicator positions for treatment of a presacral tumour;" International Journal on Hyperthermia, Feb. 2007; vol. 23, No. 1; pp. 37-47.

(Continued)

*Primary Examiner* — Kaitlyn Smith
(74) *Attorney, Agent, or Firm* — Thorpe North & Western LLP

(57) ABSTRACT

A radio frequency annular phased array hyperthermia system providing a relatively small heated focal zone in a relatively large tissue mass includes a plurality of radio frequency energy applicators in at least one ring adapted to surround the relatively large tissue mass. A bolus having a dielectric constant is positioned between the energy applicators and the tissue mass. The energy applicators operate at a frequency high enough to create the relatively small heated focal zone. The spacing between adjacent applicators in the at least one ring is less than a critical distance and spacing between adjacent rings when the at least one ring is a plurality of side by side rings is less than a critical distance with such critical distances being interdependent on the frequency of the energy radiated, the dielectric constant of the bolus, the size of the bolus, and the size of the relatively large tissue mass.

19 Claims, 33 Drawing Sheets

(56) References Cited

U.S. PATENT DOCUMENTS

2009/0306646 A1    12/2009   Turner et al.
2011/0245900 A1    10/2011   Turner et al.
2012/0172954 A1     7/2012   Zastrow et al.
2014/0012063 A1     1/2014   Turner et al.

OTHER PUBLICATIONS

Paulsen et al.; "Optimization of pelvic heating rate distributions with electromagnetic phased arrays;" International Journal on Hyperthermia, 1999, vol. 15, No. 3; pp. 157-186.

Seebass et al.; "Electromagnetic phased arrays for regional hyperthermia: optimal frequency and antenna arrangement;" International Journal on Hyperthermia, 2001, vol. 17, No. 4; pp. 321-336.

Wust et al.; "3-D computation of E fields by the volume-surface integral equation (VSIE) method in comparison with the finite-integration theory (FIT) method;" IEEE Trans Biomed Eng. (Aug. 1993); vol. 40, No. 8; pp. 745-759.

Wust et al.; "Antenna arrays in the SIGMA-eye applicator: Interactions and transforming networks;" Medical Physics, Aug. 2001; vol. 28, No. 8; pp. 1793-1805.

Wust et al.; "Electric field distributions in a phased-array applicator with 12 channels: Measurements and numerical simulations;" Medical Physics, Nov. 2000; vol. 27, No. 11; pp. 2565-2579.

EP Search Report, Paul F. Turner; Search Completed Feb. 6, 2018; dated Feb. 13, 2018; 8 Pages.

Table Comparing 3D Adjustments for Focus vs. Frequency For Sigma Eye Shape Ellipse Muscle Phantom

| Frequency (MHz) | Minor D (cm) | Major D (cm) | Length L (cm) | Volume (cc) | Muscle/Fat Ratio | P1-P5 Phase | Comments |
|---|---|---|---|---|---|---|---|
| 100 | 20 | 16 | 20 | 3351 | 1.2 | 77 | 3D focus with A-P section |
| 100 | 12.8 | 16.6 | 20.2 | 2247 | 0.9 | 48 | 3D focus not with A-P section |
| 140 | 12.0 | 12.0 | 16.4 | 1237 | 0.6 | 67 | 3D focus |
| 140 | 14.2 | 11.5 | 26.6 | 2274 | 0.65 | 33.5 | Ave of 70 AP Compensation &3D |
| 140 | 13.6 | 12.3 | 20.2 | 1769 | 1.7 | 33.5 | Ave of 70 deg AP Compensation % 3D |
| 140 | 13.1 | 11.5 | 18.7 | 1475 | 1.7 | 33.5 | |
| 175 | 7.1 | 14.4 | 17.0 | 910 | 2.8 | 48 | |
| 175 | | | | | 1.0 | 84 | Muscle surface hotspot. 33% center SAR. M/F=1.0, water bolus |
| 250 | 5.9 | 8.6 | 11.8 | 313 | 0.72 | 101 | |

Fig. 52

Table Comparing 3D Adjustments for Focus vs. Frequency For 24 Dipole Cylindrical Array and Cylindrical 28cm Diameter Muscle Phantom

| Frequency (MHz) | Minor D (cm) | Major D (cm) | Length L (cm) | Volume (cc) | Muscle Fat Ratio | P1-P5 Phase | Comments |
|---|---|---|---|---|---|---|---|
| 100 | 15.1 | 15.1 | 20.2 | 2412 | 2.2 | 38.7 | 3D 0cm focus |
| 140 | 12.7 | 12.7 | 17.7 | 1495 | 1.3 | 28 | Equal Phase |
| 140 | 15.1 | 15.1 | 16.6 | 1584 | 0.5 | 54.2 | 3D Focus |
| 175 | 9.8 | 9.8 | 15.3 | 769 | 1.4 | 68 | Muscle, 3D focus |
| 175 | 9.8 | 9.8 | 15.3 | 769 | 1.3 | 68 | 3D Focus water bolus |
| 250 | 5.8 | 5.8 | 11.7 | 206 | 2.4 | 68 | High surface heating 68deg |
| 250 | 7.4 | 7.4 | 13.6 | 390 | 2.0 | 76 | Highsurface heating 76deg. |
| 250 | 3.7 | 6.9 | 13.2 | 176 | 3.1 | 56 | Bolus |

Fig. 53

Table Comparing 3D Adjustments for Focus vs. Frequency For 24 Dipole Cylindrical Array and Cylindrical 28cm Diameter Saline Phantom

| Frequency (MHz) | Minor D (cm) | Major D (cm) | Length L (cm) | Volume (cc) | Muscle/ Fat Ratio | P1-P5 Degree Shift | Comments |
|---|---|---|---|---|---|---|---|
| 100 | 18.6 | 18.6 | 20.2 | 3659 | 1.35 | 90 | Water bolus |
| 100 | 23 | 23 | 20.2 | 5595 | 1.35 | 90 | Water bolus |
| 100 | 13.6 | 13.6 | 20.2 | 1957 | 1.35 | 38.7 | 3D focus 0cm |
| 100 | 14.9 | 14.0 | 25 | 2906 | 2.1 | 0 | Water bolus |
| 100 | 9.9 | 9.9 | 14.4 | 739 | 2.5 | 75 | Water bolus |
| 100 | 14.1 | 14.1 | 25.8 | 2682 | 2.0 | 0 | 0 phase shift |
| 100 | 15.0 | 15.0 | 25.2 | 2969 | 2.0 | 0 | 3D focus |
| 100 | 16.2 | 16.2 | 23.2 | 3189 | 2.1 | 39 | Water bolus |
| 140 | 9.7 | 9.7 | 17.7 | 876 | 2.1 | 0 | Water bolus |
| 140 | 8.5 | 8.5 | 12.9 | 488 | 1.2 | 52 | Water bolus |
| 140 | 9.0 | 9.0 | 13.0 | 636 | 9.0 | 0 | Water bolus |
| 140 | 11.0 | 11.0 | 15.4 | 976 | 0.71 | 54.2 | 3D 0cm |
| 175 | 6.9 | 6.9 | 13.4 | 334 | 2.0 | 67.6 | 3D 0cm Focus water bolus |
| 175 | 6.0 | 6.0 | 12.0 | 226 | 3.0 | 65 | Water bolus |
| 250 | 5.0 | 5.0 | 16.3 | 213 | >2.7 | 0 | Water bolus |
| 250 | 5.5 | 5.5 | 13 | 206 | 2.88 | 75.6 | Good pattern,3D Opt. focus full array size |
| 250 | 5.5 | 5.5 | 12.4 | 196 | 2.8 | 82 | |
| 250 | 5.2 | 5.2 | 19.3 | 146 | 1.6 | | Good pattern 3D, 32cm water bolus and 6.82cm dipoles Water bolus |

Fig. 54

Table Comparing 3D Adjustments for Focus vs. Frequency For 24 Dipole Sigma Eye Array and Elliptical Saline Phantom

| Frequency (MHz) | Minor D (cm) | Major D (cm) | Length L (cm) | Volume (cc) | M/F Ratio | P1-P5 Phase | Comments |
|---|---|---|---|---|---|---|---|
| 100 | 20.3 | 15.6 | 19.3 | 3201 | 0.87 | 0 | 50 deg AP Compensation water bolus |
| 100 | 20.9 | 13.1 | 22.6 | 3240 | 1.0 | 0 | 44 deg AP compensation, water bolus |
| 100 | 21 | 13.1 | 21 | 3025 | 1.42 | 0 | |
| 100 | 13.6 | 18.1 | 20.2 | 2601 | 0.78 | 48 | 3D water bolus |
| 250 | 3.9 | 5.9 | 9.7 | 117 | 1.67 | 101 | Propylene glycol bolus |
| 250 | 4.3 | 6.2 | 11.0 | 143 | 2.0 | 101 | |

Fig. 55

Penetration Depth and Focal Gain vs. Frequency
Simplified Overview of Potential For Deep Adult Torso Heating

| Freq. MHz | 1/e depth (13.5% SAR) in muscle | λ cm muscle | Focal Dia. for 3D Focusing In Muscle | Focal Gain (Depth/ volume) 100MHz reference | 50% SAR Calculated Volume | RF Channels Needed |
|---|---|---|---|---|---|---|
| 100 | 7.67cm | 29.3 | 12.8-20cm | 1 | 2400-3351cc | 12 |
| 140 | 6.9 | 22.9 | 12-16.4 | 1.6 | 1237-1584 | 12 |
| 175 | 6.0 | 20.5 | 9.8-15.3cm | 2.24 | 750-910cc | 24 |
| 250 | 5.85 | 14.4 | 5.8-11.7cm | 5.4 | 206-313cc | 24 |
| 434 | 5.17 | 8.82 | 4-8* | 7* | 124cc* | 48 |

Fig. 56

Fig. 57  Saline and Fat Dielectric Parameters used in Model

| F MHz | ε, saline | σ, S/m saline | ε, Fat | σ, S/m Fat | λ, cm saline | λ cm fat |
|---|---|---|---|---|---|---|
| 100 | 78 | 0.470 | 6.07 | 0.036 | 34.0 | 122 |
| 140 | 78 | 0.482 | 5.88 | 0.037 | 24.3 | 88.4 |
| 175 | 78 | 0.490 | 5.78 | 0.038 | 19.4 | 71.3 |
| 250 | 78 | 0.505 | 5.68 | 0.039 | 13.6 | 50.4 |
| 434 | 78 | 0.537 | 5.57 | 0.042 | 7.8 | 29.3 |

Fig. 58
Dielectric characteristics used in the phantom model. The water bolus is also modeled in accordance to published dielectric and conductivity values at 25°C.

| Frequency MHz | Wavelength in Fat | Actual Muscle dielectric (saline is 78) | 2/3$^{rd}$ Muscle conductivity S/m | Muscle Phantom Wavelength (cm) | Solid Muscle wavelength (cm) Gabriel |
|---|---|---|---|---|---|
| 100 | 110 | 66.0 | .47 | 32.2 | 29.3 |
| 140 | 82.6 | 62.7 | .482 | 24.7 | 22.9 |
| 175 | 67.9 | 61.1 | .49 | 20.5 | 15.6 |
| 250 | 49 | 59 | .505 | 15.0 | 15.6 |
| 434 | 28.9 | 56.9 | .537 | 9.0 | 9.2 |

Fig. 59 Bolus Dielectric and Wavelengths

| Freq MHz | Water | | Ethylene Glycol | | Propylene Glycol | | Alcohol | |
|---|---|---|---|---|---|---|---|---|
| | ε Dielectric | λ Wavelength | ε dielectric | λ wavelength | ε dielectric | λ wavelength | ε dielectric | λ wavelength |
| 100 | 78 | 34.0 cm | 37 | 49.3 | 26 | 58.8 | 8 | 106 |
| 140 | 78 | 24.3 | 37 | 36.2 | 26 | 42.0 | 8 | 75.8 |
| 175 | 78 | 19.4 | 37 | 28.2 | 26 | 33.6 | 8 | 60.6 |
| 250 | 78 | 13.6 | 37 | 19.7 | 26 | 23.5 | 8 | 42.4 |
| 434 | 78 | 7.83 | 37 | 11.4 | 26 | 13.6 | 8 | 24.4 |

APPARATUS AND METHOD FOR CREATING SMALL FOCUS DEEP HYPERTHERMIA IN TISSUE

PRIORITY CLAIM

Priority is claimed to copending U.S. Provisional Patent Application Ser. No. 61/990,036 filed May 7, 2014, which is hereby incorporated herein by reference in its entirety.

BACKGROUND OF THE INVENTION

Field

The present invention relates generally to systems and apparatus for irradiating targets with electromagnetic radiation, and more specifically to systems having annular-type or various sectored applicators and associated control systems for controlling application of radiation to targets through phased array power steering.

State of the Art

Current systems for applying electromagnetic radiation (EMR) to targets, such as living bodies and biological tissue, and controlling the position of a region of heating within the target through phased array power steering are provided with a plurality of electromagnetic applicators powered by multi-channel EMR systems where different applicators are each provided with electronically controlled power and electronically controlled phase for different channels of the EMR system. This creates a desired phased array heat pattern steering capability.

Several types of therapeutic treatments for cancer in humans are in current, common use. These treatments include surgery, X-rays, radiation from particle accelerators and radioactive sources, and chemotherapy. These treatments are often combined in various ways to enhance treatment effectiveness.

Although such conventional treatment techniques have been successful in treating cancer in many patients and in prolonging the lives of many other patients, they are frequently ineffective against many types of cancer and often have severe adverse side effects at the necessary treatment levels. Protracted treatment of cancer patients by X-rays or chemotherapy, as an example, tends to eventually destroy or inhibit the patients' natural immunological systems to an extent that many patients eventually succumb to common infectious diseases, such as influenza or pneumonia, which otherwise probably would not be fatal. Also, many patients having advanced stages of cancer or complications may become too weak to withstand the trauma of surgical or other cancer treatments so that therapy must be discontinued.

Due both to the prevalence and the typically severe consequences of human cancer, as well as frequent ineffectiveness of current treatments such as those mentioned above, medical researchers are continually experimenting in an attempt to discover and develop improved or alternative cancer treatment methods with their associated treatment apparatus.

Hyperthermia, the generation of artificially elevated body temperatures, has recently been given serious scientific consideration as an alternative means for cancer treatment. Much research has been conducted into the effectiveness of hyperthermia alone or in combination with other treatment methods. This research is important in that hyperthermia techniques appear to have the potential for being extremely effective in the treatment of many or most types of human cancer, without the adverse side effects which are associated with current methods for cancer treatment. Hyperthermia is sometimes called thermal therapy, indicating raising the temperature of a region of the body.

Researchers into hyperthermia treatment of cancer have commonly reported that many types of malignant growths in humans can be thermally destroyed, usually with no serious adverse side effects, by heating the malignancies to temperatures slightly below that which would be injurious to most normal, healthy cells. Furthermore, many types of malignant cell masses have reportedly been found to have substantially lower heat transfer to lessen their ability to dissipate heat, presumably due to poorer vascularity and reduced blood flow characteristics. Consequently, these types of growths appear to be more affected by the hyperthermia treatment, i.e., reach higher temperatures than tissue having normal blood flow. This is referred to as a "therapeutic gain". Poorly vascularized malignant growths can reportedly be heated to temperatures several degrees higher than the temperature reached by the immediately surrounding healthy tissue. This promises to enable hyperthermic treatment of those types of malignant growths which are more thermally sensitive than normal tissue without destruction of normal cells, and additionally to enable higher temperature, shorter hyperthermia treatment times of more thermally sensitive types of malignancies which exhibit poor vascularity.

In this regard, researchers have commonly reported that as a consequence of these thermal characteristics of most malignant growths and the thermal sensitivity of normal body cells, hyperthermia temperatures for the treatment of human cancer should be carefully limited within a relatively narrow effective and safe temperature range. Hyperthermia is generally provided by temperatures over 40 degrees C. (104 degrees F.). At treatment temperatures above approximately 45 degrees C. (113 degrees F.), thermal damage to most types of normal cells is routinely observed if the time duration exceeds 30 to 60 minutes. Thus, great care must be taken not to exceed these temperatures in healthy tissue for a prolonged period of time. The duration of exposure at any elevated temperature is, of course, an important factor in establishing the extent of thermal damage to the healthy tissue. However, if large or critical regions of the human body are heated above 45 degrees C. for even relatively short times, injury to normal tissue is likely to result. The intent of hyperthermia is to get as much of the tumor region above 40 degree C. as is possible, while not heating the normal tissue above 44 degrees C. If a more selective high temperature can be obtained in the tumor or target tissue, there will be a greater desirable amount of damage done to the tumor or target tissue.

In treating cancerous tissue, it is important to heat all of the cancerous tissue to therapeutic temperatures which can include temperatures well over 45 degrees C., with temperatures over 60 degrees C. desirable in some situations, without heating the normal tissue to temperatures which will injure the normal tissue. Greater tumor or target tissue damage can be obtained at higher temperatures. The goal of most hyperthermia systems is to be able to heat the tissue in need of treatment without heating the normal tissue surrounding the tissue in need of treatment. Therefore, to provide such treatment it is desirable to have a hyperthermia system which can provide a heating zone about the size of the tumor or other diseased tissue to be treated and it is critical to provide this heating zone at the location of the tumor or other diseased tissue to be treated. This can be particularly difficult in treating tumors or other tissue to be treated that is located deep within a relatively large mass of normal tissue, such as within a human torso, i.e., within the pelvis, abdomen, or thorax. The torso of an adult human is typically of a size having diameters between about 22 cm and 33 cm. A tumor or other tissue deposit to be treated in a human pelvis, abdomen, or thorax typically has a maximum diameter of about 8 cm or less and may be located in various positions within the pelvis, abdomen, or thorax. Most of these are located deep within the normal body tissue, as opposed to near the surface of the normal tissue (skin), and require what is referred to as "deep-heating".

Hyperthermia systems using phased arrays of radio frequency radiating applicators arranged noninvasively around an area of the body containing a tumor or other tissue to be treated, such as the pelvis, abdomen, or thorax, are commercially available. Extensive articles and reports have been written on the use of these phased array systems to provide hyperthermia heat pattern steering, and several patents have been issued covering the use of phased arrays, see, for example, U.S. Pat. Nos. 5,097,844 and 4,672,980. All of these systems rely upon the use of electronic phase and power steering to provide heat pattern focusing and steering control. When radio frequency signals are directed into a body portion from several applicators arranged around the body portion, these signals are superimposed within the body portion to provide areas of constructive interference and areas of destructive interference. The areas of constructive interference are areas of heating with maximum heating occurring where the largest number of superimposed signals constructively interfere. In a phased array hyperthermia system, the phase and amplitude of each signal is chosen so that theoretically all of the signals directed into the body will be superimposed to constructively interfere and provide maximum heating at the location of the tissue to be treated and will form a heated focal zone at that location. This heated focal zone should be of a temperature and size to heat the entire area of tissue to be treated to the desired minimum temperature for treatment while not heating surrounding tissue to an extent to cause damage to this surrounding tissue. As indicated above, it is important to limit the heating of the normal tissue surrounding the tissue to be treated. However, although not preferred, in many instances some destructive heating of normal tissue surrounding the tissue to be treated can be tolerated to ensure that all tissue to be treated is heated to the critical temperature. It is also important that hot spots that could damage normal tissue are not created in areas of normal tissue away from the tissue to be treated or away from the tissue immediately surrounding the tissue to be treated.

The BSD-2000 system produced by BSD Medical Corporation, Salt Lake City, Utah, is a radio frequency annular phased array hyperthermia system for heating deep seated tissue to be treated in a relatively large diameter tissue mass such as a human torso. The system provides three rings of multiple radio frequency applicators, such as radio frequency dipole antennas or radio frequency dipole antenna pairs, with the applicators of each ring spaced around an opening adapted to receive therein the body portion having the tissue to be treated. The respective rings are spaced or stacked along the longitudinal axis of the body portion having the tissue to be treated. Separate power channels control the frequency, radiated power, and relative phase of the radio frequency energy radiated by each applicator or combination of selected applicators. Such a system is described in U.S. Pat. No. 5,097,844. Each channel is connected to an antenna or an antenna pair in the array and has separate electronic controls for the power and phase of the radio frequency signal sent to the connected antenna, antenna pair, or combination of selected antennas or antenna pairs. This allows electronic steering and focusing of the heating pattern. The most advanced phased array applicator configuration currently used with this system is called the "Sigma Eye", and contains three rings of dipole antennas as described in U.S. Pat. No. 5,097,844. However, rather than circular rings as shown in U.S. Pat. No. 5,097,844, the rings of the Sigma Eye applicator are elliptical in shape. The Sigma Eye elliptical rings provide improved comfort for patients over circular rings and maximizes the 3D energy convergence at the targeted treatment location. The use of three rings of applicators allows three dimensional steering and focusing of the heating zone created by the antenna array. U.S. Pat. No. 4,672,980 teaches a system having an antenna array containing two rings of dipole antennas to provide two dimensional steering and focusing of the heating zone created by that antenna array. It should be noted that in the present application, as shown by the Sigma Eye configuration disclosed, "ring" is not used to mean circular, but to mean a plurality of applicators spaced around an opening adapted to receive a body part so that with a body part received in the opening the applicators of the ring are spaced around the body part in a manner to direct the radio frequency signals into the body part. The rings can take various configurations, which can be, for example, a circular configuration, an elliptical configuration, a rectangular configuration, a triangular configuration, or other configuration surrounding the tissue to be heated. Similarly, while such systems are generally referred to as annular phased array systems, the use of the term "annular" does not limit the system to circular arrays but to arrays having any shape as indicated above for the meaning of ring.

Prior art phased array systems have successfully used radio frequency signals up to 120 MHz to provide deep heating of tissue in the human torso which includes the pelvis, abdomen, and thorax. The commercial BSD-2000 system using the Sigma Eye as described above has been limited to use of radio frequency signals no greater than 100 MHz when used for deep heating. This frequency limit was chosen in order to provide sufficient penetration of the radiation deep into the tissue to provide a controlled heated focal zone deep in the tissue without producing hot spots in other parts of the tissue away from the heating zone. In order to obtain optimum localization of heating at depth it is necessary to use a frequency low enough to have sufficient penetration and limit the formation of standing waves that could produce hot spots in the tissues away from the desired heated focal zone. There is no data indicating that a frequency above 100 MHz can provide an adequate deep central heated focal zone in the relatively large tissue mass of the adult torso. Also, it was expected that the use of higher frequencies would have the potential for creating multiple hot spots within the normal tissue away from the desired heated focal zone due to the standing waves. The current BSD-2000 system uses a maximum operating frequency of 100 MHz for deep body heating and uses 12 RF power and phase control channels to drive 12 pairs of linear dipole antennas as described in U.S. Pat. No. 5,097,844. This system provides deep heating of the pelvic, abdominal, and thorax regions of an adult with a heated focal zone volume of 1,500 to 5,000 cubic centimeters at a frequency of 100 MHz. The 1,500 cc volume corresponds to a primary heating volume with a diameter of 14 cm in each of the three orthogonal axes. However, as indicated above, most target tumors deep in the body are much smaller than this size, typically with a diameter of less than 8 cm. Using frequencies at or below 120 MHz in a noninvasive antenna array system forms a spherical focus for the heated focal zone which has a major axis diameter of 20 cm or greater. When the focus is spheroidal, using frequencies no greater than 120 MHz, it is possible to lessen one dimension to as small as 10 cm, but then the other maximum diameter dimension is greater than 20 cm. This is much larger than the typical size of the tissue needing heat treatment so substantial volumes of normal tissue around the deposit to be treated will also be heated and damaged. The use of higher frequency RF signals can theoretically reduce the size of the heating zone produced by the interacting signals. Some reports have indicated that frequencies as high as 434 MHz have been used with annular type phased array systems for producing smaller heating zones in body parts such as limbs or the neck region of a body. Such high frequencies can be used in these regions due to the much smaller total tissue mass size for these regions of the human body. With these smaller sized body parts, deep tissue penetration is not needed.

While the U.S. Pat. No. 5,097,844 discloses that the theoretical focal zone size can be reduced by using higher frequencies, it does not disclose how such a system could be implemented to provide a small and deep focal zone size and a selectively heated focal zone at depth in the tissue. Further, the patent does not disclose how the deep local heated focal zone could be preserved when phase and amplitude steering is done to direct the smaller heated focal zone to a targeted treatment site. Therefore, there is a need to develop a means to utilize higher operating frequencies to reduce the size of the heated focal zone. To accomplish this requires special design considerations and limitations that were not foreseen or included in U.S. Pat. No. 5,097,844. The higher frequencies have not been used in prior art systems for deep tissue heating. The inventors have found that the use of higher frequencies to enable smaller heated focal zones in deep tissue heating require special design constraints for the annular phased arrays and changes in the bolus interface media between the applicator array and the human body. The dependence of body size, the size of the targeted tissue, the array size, the array shape, the number of radiating applicators, the number of independent RF power and phase control channels, the bolus interface media, and the operating frequency must all be considered in the design in order to achieve a desired selective deep heated focal zone.

There is a need for EMR applicator apparatus, and corresponding methods for EMR irradiation, which provide a more localized deep focal heating of deep tumors or otherwise diseased tissues in the body and to provide more selective target tissue heating with reduced heating of other normal tissues. The need is that the heating zone should penetrate to the center of the torso of an adult body and be capable of selective heating in a targeted region that is approximately 8 cm in diameter or less. Thus, at all points within a sphere with a diameter of 8 cm, corresponding to a volume of 270 cubic centimeters of tissue, the relative SAR (Specific Absorption Rate, or absorbed power per unit mass) would be within 50% of the maximum SAR within the sphere of targeted tissue. It is not necessary that the heating zone be completely confined to the tumor target area, but that there is greater localization than currently available to minimize the excessive heating of normal tissues. If more selective deep heating is provided, it is expected that the target tissue could be heated to a higher temperature than is currently possible, thereby increasing the therapeutic benefit of the hyperthermia treatment without increasing toxicity to the body.

SUMMARY OF THE INVENTION

According to the present invention, an array of electromagnetic radiator applicators is utilized to surround the body of an adult size tissue mass and operated at a frequency range of 200 to 300 MHz, or greater, with a currently preferred frequency being about 250 MHz. The radiator applicators may be antennas of a dipole or equivalent radiator type. One preferred method is to have the antennas designed to radiate a linearly polarized electric field that is aligned with the body central axis. Such a configuration is described in U.S. Pat. Nos. 5,097,844 and 4,672,980. The space between the antennas and the body is filled with the customary bolus having a bolus media therein. The bolus media has a dielectric constant which is much greater than 1. However, for use with higher frequency radiation signals, the bolus media must also have a dielectric constant which is lower than that of water which is 78 to minimize superficial hot spots and also preserve a deep selective central focus with a practical number of antennas and control channels. The use of the correct bolus media is needed to avoid undesirable hot zones along the tissue surface that both would limit patient tolerance and also reduce the deep penetration capability. At a frequency of 250 MHz the wavelength in muscle tissue is 14.4 cm. If this was used on a tissue mass with a cross-sectional diameter of 22 cm to 33 cm, the diameter to wavelength ratio would be 1.53 to 2.3. For a tissue diameter of 28 cm the diameter to wavelength ratio would be 1.94 at 250 MHz. This frequency selection for adult body torso sizes is beyond that practiced in previous art. To provide the conditions of a phased array necessary to operate at such a high frequency, it has been found that there are critical applicator position and array sizes needed to avoid creation of high secondary hot spots in tissue away from the targeted tissues. The design of such an array requires a maximum spacing between antennas that are adjacent along a circumferential path (ring) around the tissue mass containing the tissue in need of treatment that is not more than 0.8 of the wavelength of the radio frequency signal at the operating frequency in the bolus media. Further, the maximum difference in phase at a bolus-tissue mass interface point between a radiated signal traveling through the bolus between the center of a radio frequency energy radiator applicator and the center of the tissue mass and a signal traveling through the bolus to that point from the center of an adjacent radio frequency energy radiator applicator should be no more than 135 degrees. This phase difference can be predetermined for the size of body tissue mass containing the tissue to be heated in relation to the size, shape, and positioning of the antennas of the array and the size of the bolus and the characteristics of the bolus media. When using a 3D focusing system such as described in U.S. Pat. No. 5,097,844 using three or more stacked antenna rings, the distance between adjacent stacked antennas (between adjacent antenna rings) should be no more than 0.8 of the wavelength of the radio frequency signal at the operating frequency in the bolus material, and the difference in phase at the bolus-tissue mass interface between signals from the center of aligned stacked radio frequency energy radiator applicators mid way between the rings is no more than 125 degrees. The dielectric of the bolus media also sets a limit to the position and spacing of the long axis stacked antennas for a particular frequency and tissue size.

The prior art has not considered the special limitations and constraints needed to implement a high frequency phased array that will be capable of producing a heated focal zone of volume and diameter not much larger than the typical deep tissue tumor to be treated and with adequate penetration depth to adequately heat such deep seated tissue. Improper selection of the applicator array design can result in less penetration depth, high superficial hotspots, degraded penetration when phase steering the heated focal zone, excess superficial fat heating, multiple hotspots, and an elongated shape in the deep energy and heated focal zone.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIGS. 52-59 are various tables showing test results from various system operations and showing various parameters used.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

The invention includes the recognition that at least four variables in a phased array radio frequency (RF) hyperthermia system are interdependent and critical to being able to produce a desired size of heating zone deep within a tissue mass containing a zone within the tissue mass to be heated to a desired minimum temperature while maintaining other tissue within the mass below such minimum temperature. The invention also includes specific arrangements of the parts of a phased array radio frequency hyperthermia system based upon the variables and interaction between the variables by which a relatively small heating zone, such as the size of a typical tumor, can be produced by such a system in a relatively large tissue mass such as represented by a human pelvis, abdomen, or thorax. As used herein, a relatively large tissue mass will be a three dimensional tissue mass having a cross sectional diameter of at least about 15 cm, which is larger than the head and neck area of most humans, but includes the pelvis, abdomen, and thorax of most humans which usually between about 22 cm to about 33 cm. A relatively small heating zone will be a zone large enough to encompass a typical tumor occurring in a human pelvis, abdomen, or thorax, which will typically have a cross sectional diameter of about 8 cm or less, and small enough so that a substantial volume of normal tissue surrounding the tumor will not be heated to tissue damaging temperatures. For purposes of the present invention, a relatively small heating zone will have diameters of less than about 14 cms.

Figure 1:
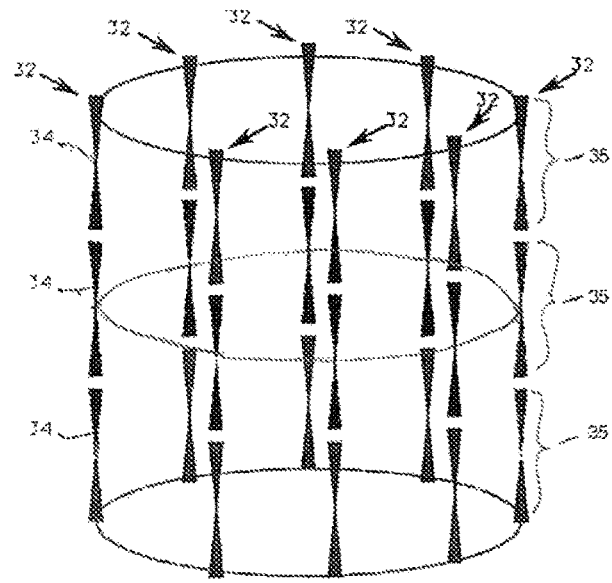
FIG. 1 is a view showing a cylindrical arrangement of groups of dipole antennas forming an electromagnetic applicator of the prior art 3-D hyperthermia system of U.S. Pat. No. 5,097,844.
Figure 2:
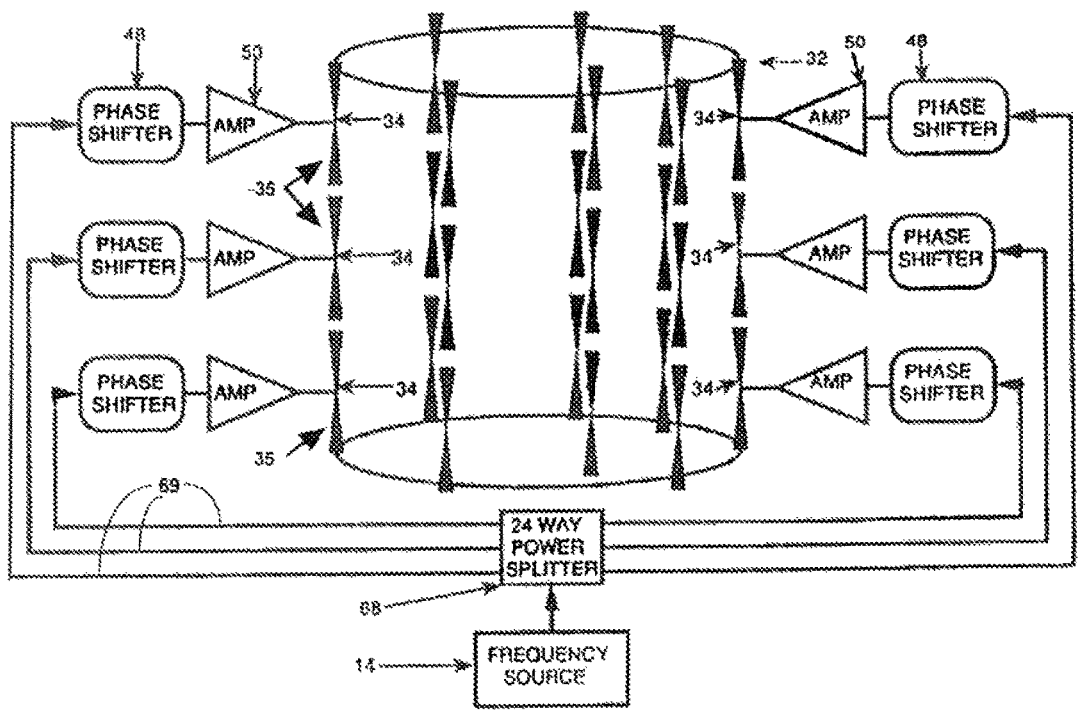
FIG. 2 is a schematic view showing in partial block form a prior art power connection arrangement for the dipole antennas of FIG. 1.

As indicated in the above State of the Art section, a phased array radio frequency hyperthermia system that allows for electronic steering and focusing of the heating pattern created by the system is shown and described in U.S. Pat. Nos. 5,097,844 and 4,672,980, both incorporated by reference herein in their entirety. The system as described in said U.S. Pat. No. 5,097,844 will be used as the illustrated example of an annular phased array radio frequency hyperthermia system for purposes of explaining the current invention. FIG. 1 herein is similar to FIG. 2 of said U.S. Pat. No. 5,097,844 and shows a 3-D cylindrical antenna array consisting of three rings 35 each including a plurality of, here shown as eight, applicators in the form of dipole antennas 34. The rings 35 are spaced or stacked side-by-side with the respective antennas 34 of each ring aligned end to end along the direction of the E-field polarization axis which is also the longitudinal axis of a tissue mass when placed inside of the rings. Each of the three end to end aligned antennas 34 is indicated as an antenna group 32. While various types of antennas can be used, FIGS. 1 and 2 show the antennas in the form of dipole antennas made of tapered metallic conductive strips with the RF power feed located midway between the two strips forming the dipole. The taper is increased outwardly from the central feed point to increase the frequency bandwidth and the near field energy along the region of the tips of the dipoles. The length of the dipoles should be determined in light of the operating frequency to prevent loss of energy. With each ring 35 having eight antennas 34, the three rings together have a total of twenty four antennas.

Figure 8:
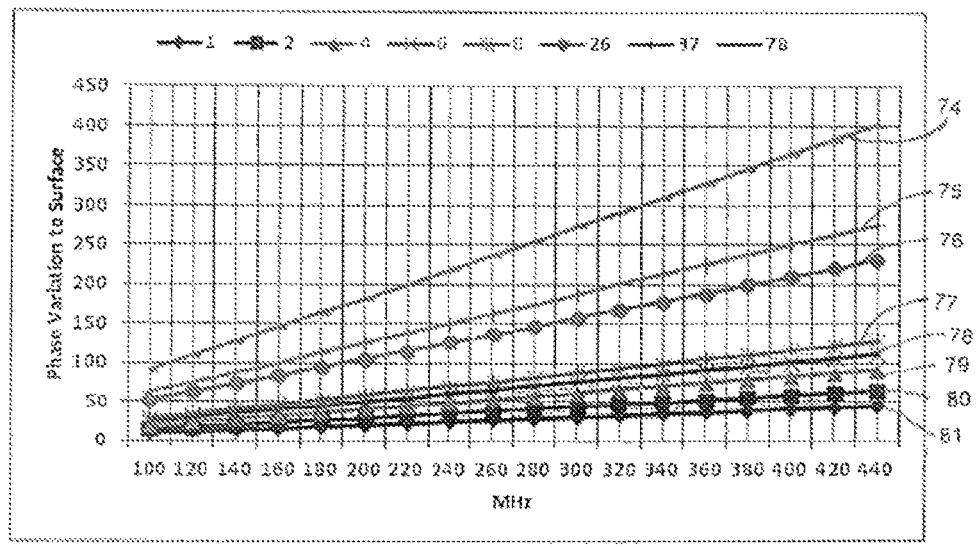

FIG. 2 herein is similar to FIG. 8 of said U.S. Pat. No. 5,097,844 and shows a twenty four amplifier system providing independent control of each antenna of the antenna array of FIG. 1. A twenty four way power splitter 68 is connected to a source of radio frequency power 14 of a particular selected frequency and provides a separate radio frequency power signal 69 for each of the twenty four dipole antennas shown in FIG. 1. While only six separate radio frequency power signals 69 from twenty four way power splitter 68 are shown in FIG. 2, and while, for clarity, FIG. 2 just shows the connection of the radio frequency signals 69 from the power splitter 68 connected to the three individual antennas 34 of two opposite antenna groups 32, there are twenty four such separate radio frequency power signals 69 transmitted from twenty four way power splitter 68. Each of the separate radio frequency power signals 69 is connected to a phase shifter 48. Each phase shifter 48 controls the phase of the power applied to an amplifier 50. Each amplifier 50 is connected to one of the twenty four dipole antennas 34 and provides the increase in signal power (gain) necessary for the particular dipole antenna 34 to which it is attached. While six of the connections described are shown in FIG. 2, similar connections are made for each of the antennas 34 in each of the antenna groups 32. It should be noted that since all twenty four radio frequency power signals 69 originate from a single signal power source 14, all twenty four radio frequency power signals 69 have exactly the same frequency.

Figure 3:
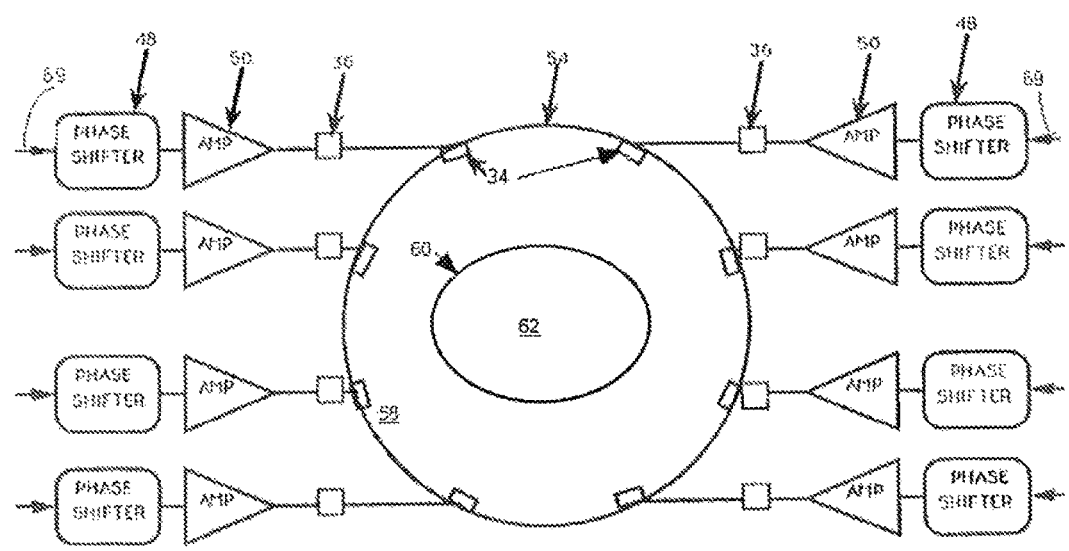
FIG. 3 is a partial schematic view showing in block form the power connection arrangement of FIG. 2 for one of the three stacked rings of the dipole antennas.
Figure 6:
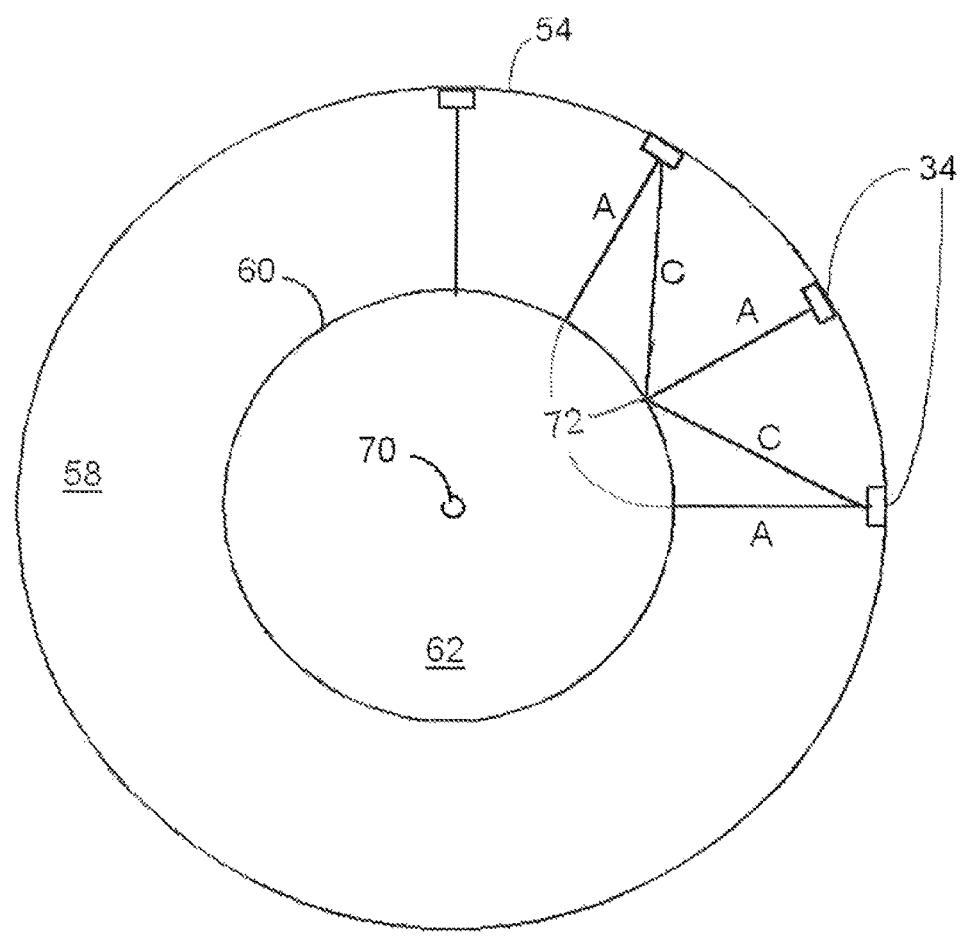
FIG. 6 is a horizontal section through an antenna ring and tissue mass centered therein showing selected signal paths from applicators through the bolus to the bolus-tissue surface interface.

FIG. 3 is similar to FIG. 6 of said U.S. Pat. No. 5,097,844 and shows the eight separate antennas 34 of one of the three stacked rings 35 of antennas shown in FIGS. 1 and 2. Each of the three rings 35 is similar. FIG. 3 shows the connections from the power splitter 68 to each of the eight antennas 34 in one of the three rings. Again, a separate radio frequency power signal 69 from the twenty four way power splitter 68 shown in FIG. 2 is connected to each of the eight phase shifters 48 shown in FIG. 3. Each phase shifter 48 controls the phase of the power applied to an amplifier 50. Each amplifier 50 is connected to one of the eight antennas 34 of the ring and provides the increase in signal power (gain) necessary for the particular dipole antenna 34 to which it is attached. With the arrangement shown in FIGS. 1-3, the phase and amplitude of the radio frequency signal to each of the dipole antennas 34 can be independently controlled to provide maximum flexibility in being able to control the steering and focus of the heated focal zone for the hyperthermia system.

Figure 4:
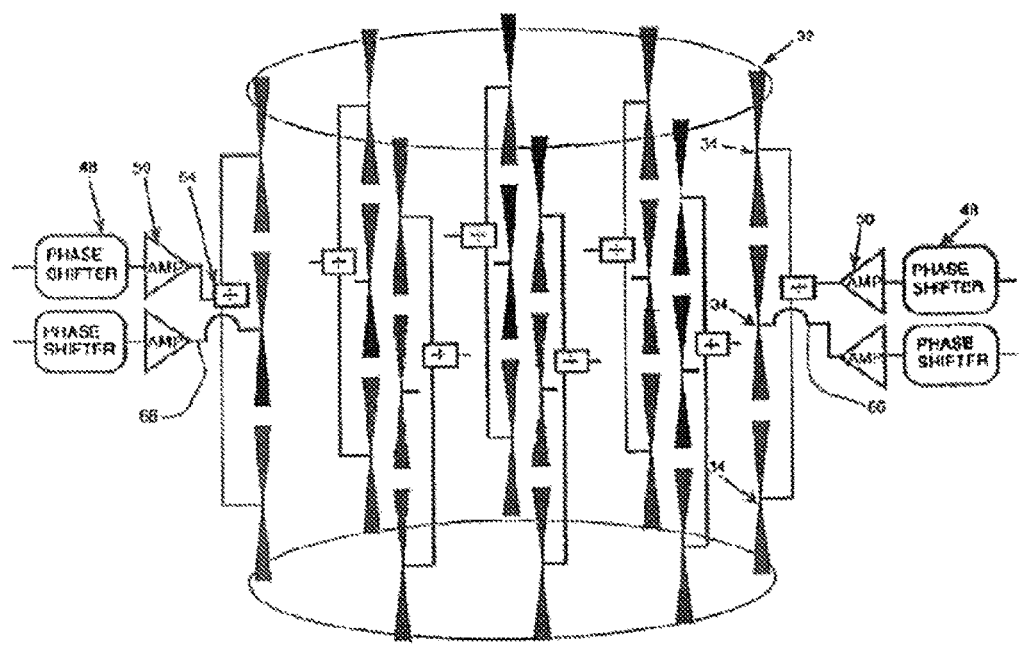
FIG. 4 is a partial schematic view similar to that of FIG. 2 showing in partial block form a different prior art power connection arrangement for the dipole antennas of FIG. 1.

While the hyperthermia system shown in FIGS. 1-3 as an illustrated example of a system usable for the present invention has independent phase and amplitude control of each antenna, the system can be arranged so that groups of antennas can be connected together to a single amplifier 50 so that the phase and amplitude for a group of antennas is controlled together. Examples of such arrangements are shown in U.S. Pat. No. 5,097,844. One such arrangement usable with the current invention is shown in FIG. 4. As shown in FIG. 4, the opposite end antennas 34 of each stacked group 32 of end to end antennas are connected through a splitter 64 to a common amplifier 50. Thus, each of these opposite end antennas of a group 32 receives a signal of the same or fixed relative phase and amplitude. When groups of antennas are connected together to a single amplifier 50, the number of separate radio frequency power signals required is reduced. Thus, for the system of FIG. 4, only a sixteen way power splitter is required rather than the twenty-four way power splitter shown in FIGS. 1-3. The capabilities of a system with groups of antennas connected to the same amplifier will generally be less that when each antenna is separately controllable as with the system of FIGS. 1-3. Also, with most arrangements used with the higher frequency signals of the system of the invention, separate control of at least twenty four separate antennas will be required.

As explained in U.S. Pat. No. 5,097,844, the dipole antennas 34 of the system may be formed along the inside wall of a clear plastic or dielectric cylinder 54 using well known adhesives or metal deposition processes. A thin patch of dielectric coating material can cover each of the antennas 34. A bolus 58 can be formed within the cylinder 54 by attaching a membrane 60 having ends sealed to the cylinder 54. A fluid input/output valve, not shown, can be mounted in the cylinder 54 for inflating the bolus with fluid, which fluid will also be referred to as the bolus media. The inflated bolus defines the body area in which the body (tissue mass) 62 containing the tissue to be heated is positioned, and provides an interface with the outer surface of the tissue mass. The bolus also provides surface tissue cooling, energy confinement, and improved antenna group coupling to the tissue of the body 62 in the body area. The fluid taught as used in the bolus in U.S. Pat. No. 5,097,844 is a high dielectric low loss fluid such as deionized water. U.S. Pat. No. 5,097,884 says that in practicing the invention it is important to take into account the dielectric characteristics of the bolus region and the body when planning the activation phase of the individual antennas 34. When using a bolus filled with deionized water, the deionized water has a dielectric constant very close to that of high water tissues such as muscle or tumor tissue. The use of deionized water improves the impedance match between the antennas 34 and the tissue in the body area 62. At the frequencies of interest, the impedance of the typical body tissue is approximately 44 ohms. The impedance of the antennas 34 and other electrical portions of the system is preferably 50 ohms in order to be compatible with standard components. The impedance of deionized water at the frequencies of interest is also approximately 44 ohms, so that all parts of the system are inherently closely matched.

The wavelength $\lambda$, of electromagnetic radiation propagating in a lossy medium, is given by the following expression $$\beta := \sqrt{2} \cdot \pi \cdot f \cdot \frac{\sqrt{\varepsilon r}}{c} \cdot \sqrt{1 + \left(\frac{sigef}{2 \cdot \pi \cdot f \cdot epso \cdot \varepsilon r}\right)^2} + 1$$

$$\lambda := 2 \cdot \frac{\pi}{\beta}$$

Where f is the frequency in MHz, sigef is the media conductivity in S/m, $\varepsilon r$ is the relative permittivity of the media, epso is $8.854 \times 10^{-12}$ F/m, $\lambda$, is the wavelength in m, and c is the speed of light in vacuum, in m/s.

In proper operation of the phased array radio frequency hyperthermia system, the phase and amplitude of the radio frequency signals from each of the antennas need to be set so that the signals all arrive in phase at the desired heated focal zone location. This results in the signals constructively combining at this location. The phase of the signals radiated from the dipoles determines the location of the heated focal zone within the body. As dipoles have a wide pattern the heated focal zone is where the same phases exist in the superimposed beams. At the other points in the superimposed beams the phase is different and the energy partially cancels. In order to properly set the phase of the radio frequency signals radiated from respective antennas, the length of the signal paths between the respective antennas and the center of the desired heated focal zone need to be determined. Once the length of the signal paths is determined, the proper phase adjustments can be determined. The lengths of the signal paths can be approximated by representing the body 62, FIG. 5, having the desired heated focal zone therein, as a circular cylinder coaxial with the z-axis and having radius R from the z-axis to the outer surface of the body represented by bolus membrane 60. Let point P1 $(x_1,y_1,z_1)$ be the target point located within the body 62, and point P2 $(x_2,y_2,z_2)$ be the feed-point of the dipole antenna located on the dielectric cylinder 54 in the bolus space 58 outside of the body. The permittivity of the body and the bolus are given by $\varepsilon_1$ and $\varepsilon_2$, respectively.

Allowing for refraction, a ray propagating between P1 and P2 will pass through the outer surface of the body at point P3 $(x_3,y_3,z_3)$. By reciprocity, we consider the rays from P1 to P3 and from P3 to P2 to be given by the following vectors, where the parameter $0<t<1$ through the transit:

$$\vec{S}_1 = [x_1+(x_3-x_1)t]\hat{x} + [y_1+(y_3-y_1)t]\hat{y} + [z_1+(z_3-z_1)t]\hat{z} \quad (1)$$

$$\vec{S}_2 = [x_3+(x_2-x_3)t]\hat{x} + [y_3+(y_2-y_3)t]\hat{y} + [z_3+(z_2-z_3)t]\hat{z} \quad (2)$$

The outward going normal to the cylinder at point P3 is given by $$\vec{N} = x_3\hat{x} + y_3\hat{y} \quad (3)$$

The corresponding unit vectors are given by $$\hat{s}_1 = \frac{(x_3-x_1)\hat{x}+(y_3-y_1)\hat{y}+(z_3-z_1)\hat{z}}{\sqrt{(x_3-x_1)^2+(y_3-y_1)^2+(z_3-z_1)^2}} \quad (4)$$

$$\hat{s}_2 = \frac{(x_2-x_3)\hat{x}+(y_2-y_3)\hat{y}+(z_2-z_3)\hat{z}}{\sqrt{(x_2-x_3)^2+(y_2-y_3)^2+(z_2-z_3)^2}} \quad (5)$$

$$\hat{n} = \frac{x_3\hat{x}+y_3\hat{y}}{\sqrt{x_3^2+y_3^2}} \quad (6)$$

But the cosines of the angles of incidence and refraction are given by $$\hat{n} \cdot \hat{s}_1 = \cos(\theta_1)$$

$$\hat{n} \cdot \hat{s}_2 = \cos(\theta_2) \quad (7) \& (8)$$

Thus, using Snell's law of refraction, we derive the following equation:

$$\sqrt{\varepsilon_1}\sqrt{1-(\hat{n}\cdot\hat{s}_1)^2} = \sqrt{\varepsilon_2}\sqrt{1-(\hat{n}\cdot\hat{s}_2)^2} \quad (9)$$

Equation (9) is solved iteratively with trial values of $x_3$, $y_3$, $z_3$ subject to the constraint that $$x_3^2 + y_3^2 + z_3^2 = R^2 \quad (10)$$

Then the calculated values of $x_3$, $y_3$, $z_3$ are used in Eq. (11) to determine the transit time T, so that the required phase lag may be determined.

$$T = \sqrt{\varepsilon_1\mu_0}\sqrt{(x_3-x_1)^2+(y_3-y_1)^2+(z_3-z_1)^2} + \sqrt{\varepsilon_2}\sqrt{(x_2-x_3)^2+(y_2-y_3)^2+(z_2-z_3)^2} \quad (11)$$

Figure 5:
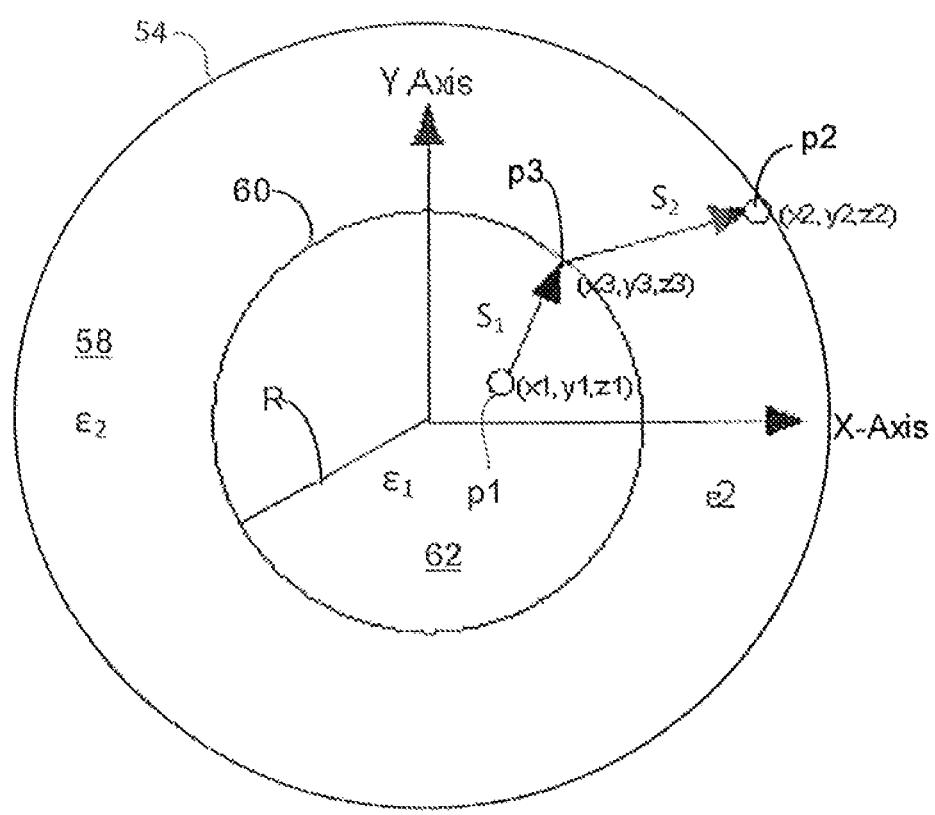
FIG. 5 is a horizontal section through an antenna ring and tissue mass centered therein showing a signal path from an applicator through the bolus and into the tissue mass to a focus zone therein.

It should be noted that the amount of refraction shown in FIGS. 5 and 6 is exaggerated for illustration purposes and generally will not be as great as shown. Further, when using a bolus filled with deionized water, the deionized water has a dielectric constant very close to that of high water tissues such as muscle or tumor tissue so there is very little refraction at the bolus-tissue interface, point P3.

The current state of the art is to select an operating frequency for the deep-heating phased array that has a wavelength long enough to avoid secondary standing waves within the tissue cross-section and that will provide deep penetration capability. For example, consider a circular cylinder having a diameter of 22 to 33 cm as a model to approximate the torso of an adult human. At a frequency of 100 MHz the wavelength in high water tissues such as muscle or tumor tissue is 29.3 cm. Thus, the ratio of the diameter of the torso tissue to the wavelength of the radio frequency signal in the tissue is 0.75 to 1.13 of a wavelength for the diameters of 22 and 33 cm, respectively. This avoids the potential for creating secondary standing waves that can create secondary heating peaks that would be away from the intended target tissue P1. However, at a frequency of 250 MHz the wavelength in high water tissues such as muscle or tumor tissue is 14.4 cm. If this higher frequency is used with a tissue diameter of between 22 and 33 cm, the ratio of the diameter of the torso tissue to the wavelength of the radio frequency signal in the tissue 1.53 to 2.3 of the wavelength. With this larger diameter tissue, creation of secondary heating peaks away from the intended target tissue is likely when using the shorter 250 MHz wavelength. This is why the commercial Sigma Eye phased array of the BSD-2000 system has a set maximum frequency of 100 MHz. While a high frequency of 434 MHz has been used in a radio frequency annular array hyperthermia system when the tissue portion of the body being treated is a neck portion of the body, the typical adult tissue diameter of the neck portion is about 12 cm. The wavelength in muscle tissue at 434 MHz is 8.8 cm. At 12 cm, the ratio of the diameter of the neck tissue to the wavelength of the radio frequency signal in the neck tissue is 1.37 of the wavelength. While close, this generally avoids the potential secondary heating peaks that would be away from the intended target tissue. However, if the 434 MHz frequency is used with a tissue diameter of between 22 and 33 cm, the ratio of the diameter of the tissue to the tissue wavelength is 2.5 to 3.75, respectively, of the shorter wavelength. With this larger diameter tissue, creation of secondary heating peaks away from the intended target tissue is likely when using the shorter 434 MHz wavelength. Adding more antennas and the number of RF control channels as well as a bolus dielectric lower than that of water and meeting the conditions of the current invention might reduce or eliminate the creation of the secondary heating peaks.

While U.S. Pat. No. 5,097,844 indicates that the normal frequency range for the system described in the patent for treating the torso portion of an adult is between about 50 to 1000 MHz and that it is most useful between about 60 to 220 MHz, as indicated above, the actual prior art systems are not operated above 120 MHz for heating tissue in the torso portion of the body. This is true even though U.S. Pat. No. 5,097,844 recognizes that these lower frequencies limit the precision to which the tissue can be selectively heated and that increasing the frequency would provide higher precision for the focusing. The diameter of the heated focal zone in the cylindrical plane is approximately between $\frac{1}{3}^{rd}$ to $\frac{1}{2}$ of a tissue wavelength. As previously indicated, most tumors in the torso portion of a human body are less than 8 cm. The need is that the heated focal zone should be able to penetrate to the center of the body of an adult torso and be capable of selectively heating targeted tissue to be heated that is approximately 8 cm in diameter or less. Selectively heating the targeted tissue means that the targeted tissue will be heated to the desired treatment temperature while the tissue surrounding the targeted tissue will not be heated to an extent that will damage such tissue. Thus, ideally, where the targeted tissue is about 8 cm in diameter, the heated focal zone produced by the annular phased array system will be about 8 cm in diameter without extending substantially beyond the 8 cm diameter. With such a system, this means that at all points within a sphere with a diameter of 8 cm, corresponding to a volume of 270 cubic centimeters of tissue, the relative SAR (Specific Absorption Rate, or absorbed power per unit mass) would be within 50% of the maximum SAR in the tissue within the sphere. The relative SAR for tissue outside of the sphere will be less than 50% of the maximum SAR in the tissue within the sphere. It is not necessary that the heated focal zone be completely confined to the tumor, but that there is greater localization or selectivity and less damaging heating of tissue outside of the diameter of the tumor or other diseased tissue to be treated than currently obtained in the current use of the radio frequency annular array hyperthermia systems with frequencies limited to 120 MHz. The smaller heating zone would minimize the excessive heating of normal tissues. If more selective deep heating is provided, it is expected that the target tissue could be heated to a higher temperature than is currently possible, thereby increasing the therapeutic benefit of the hyperthermia treatment without increasing toxicity to the body. At 250 MHz the wavelength in high water content tissue such as tumor or muscle is 14.4 cm so the focus diameter expected in the cylindrical plane would range from 4.8 to 7.2 cm. The expected long axis diameter of the central focus when optimized phase values are selected for the various antennas ranges from ½ to ¾$^{th}$ of a tissue wavelength. For 250 MHz the 50% SAR expected long axis diameter (usually along the longitudinal axis of the tissue mass) would be from 7.2 to 10.8 cm. depending on the phase settings for optimal focusing.

The inventors have found that in order to increase the frequency used in an annular phased array radio frequency hyperthermia system to thereby reduce the size of the heated focal zone produced by the system within a relatively large tissue mass containing the tissue to be treated without creating undesirable hot spots in the normal tissue of the tissue mass away from the tissue to be treated and without creating undesirable hot zones along the tissue surface that would both limit patient tolerance to the treatment and reduce the deep penetration capability for such high frequency signals, a number of parameter adjustments not disclosed in U.S. Pat. No. 5,097,844 or other prior art, are required. These adjustments include the spacing between the antennas surrounding the body, which affect the number of antennas used, the size of the bolus, and the bolus media used in the bolus. All of these are interdependent and are dependent on the frequency used. These parameters and their interdependence will be described for use with an example frequency range between 200 MHz and 300 MHz used to produce a heated focal zone sized to treat a tumor or other tissue deposit having a major diameter of 8 cm or less located in an adult human torso, such as in a human pelvis, abdomen, or thorax. The example parameters are applied to the radio frequency annular array hyperthermia system as shown and described for FIGS. 1-3 with independent control of the phase and amplitude of the signal radiated by each antenna. It has been found that while the bolus media in the bolus needs to have a dielectric constant which is much greater than 1, as does the deionized water taught in U.S. Pat. No. 5,097,844 which has a dielectric constant of 78, that for use with the higher frequencies, the bolus media must have a dielectric constant which is lower than that of water which is 78. The lower dielectric constant media is necessary at these higher frequencies to minimize superficial hot spots and to also preserve a deep selective central focus with a practical number of antennas and control channels. The use of the correct bolus media is needed to also avoid undesirable hot zones along the tissue surface that both would limit patient tolerance and also reduce the deep penetration capability.

At a frequency of 250 MHz the wavelength in muscle is 14.4 cm. When used on tissue with a cross-sectional diameter of 22 cm to 33 cm the ratio of the tissue diameter to the tissue wavelength is 1.53 to 2.3. For a tissue diameter of 28 cm the diameter to wavelength ratio is 1.94 at 250 MHz. To provide the conditions of a phased array necessary to operate at such a high frequency the inventors have found that the array requires a maximum spacing between antennas that are adjacent along a ring that is not more than 0.8 of a wavelength in the bolus media. Further, the maximum difference in phase between adjacent antennas is 135 degrees at a common circumference point at the body surface (interface between the body surface and the bolus membrane) when the radio frequency signals are directed from the array applicators to the center of the tissue mass. This difference in phase can be predetermined for the size of body to be heated in relation to the size, shape, and positioning of the antennas of the array and the dielectric constant of the bolus media.

FIG. 6 is a representation of the cylinder 54 through one of the three stacked rings with eight antennas 34 evenly spaced around the inside of the cylinder 54 with a bolus 58 formed by membrane 60 attached at its ends to cylinder 54 to define a body area 62, shown here as cylindrical as in FIG. 5 for the cylindrical body used as a model for calculations rather than ellipsoidal as in FIG. 3, which is representative of the "Sigma Eye" configuration and is more representative of a human torso. The line 60 showing the membrane also represents the surface of the body surrounded by the bolus. The bolus 58 is filled with bolus media having a dielectric constant. In FIG. 6, the desired heated focal zone, which here is at the center of the body (the tissue mass having the tissue to be treated therein), the center of which is indicated as 70, is in the center of the array. The distance through the bolus from the center of an antenna 34 to the surface of the body 62 along a line from the antenna 34 to the center 70 of the body, indicated by points 72, is indicated by A. The distance through the bolus to a point 72 from the center of an adjacent antenna 34 is indicated by C. Examples of these distances when using eight antennas spaced evenly around the outer circumference of the bolus and having a 28 cm diameter body 62, are, for a 60 cm outer bolus diameter, A=16 cm and C=24 cm, for a 44 cm outer bolus diameter, A=8 cm and C=17 cm, and for a 36 cm outer diameter bolus, A=4 cm and C=14 cm. It has been found that the difference between the phases of the radio frequency signals at a point 72 on the surface of the tissue 62 directly from an antenna, distance A, and from an adjacent antenna, distance C, should be no more that 135 degrees. The wavelength of a particular frequency of signal in the bolus depends upon the dielectric value of the bolus, i.e., the dielectric value of the media filling the bolus.

Figure 7:
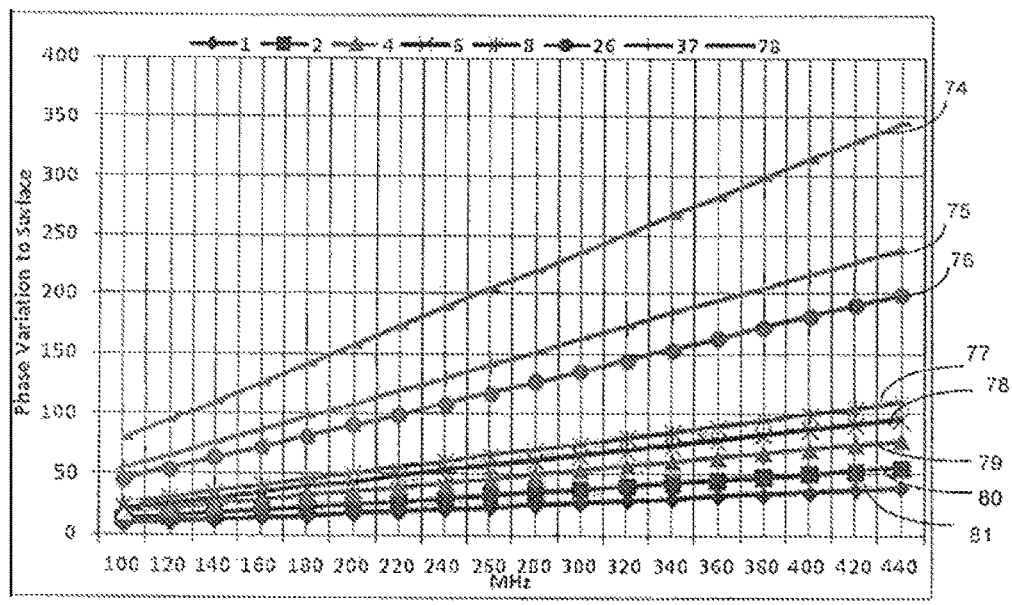
FIGS. 7-9 are graphs showing how the phase difference between the A and C distances shown in FIG. 6 changes with respect to frequency and dielectric constant and size of the bolus.
Figure 9:
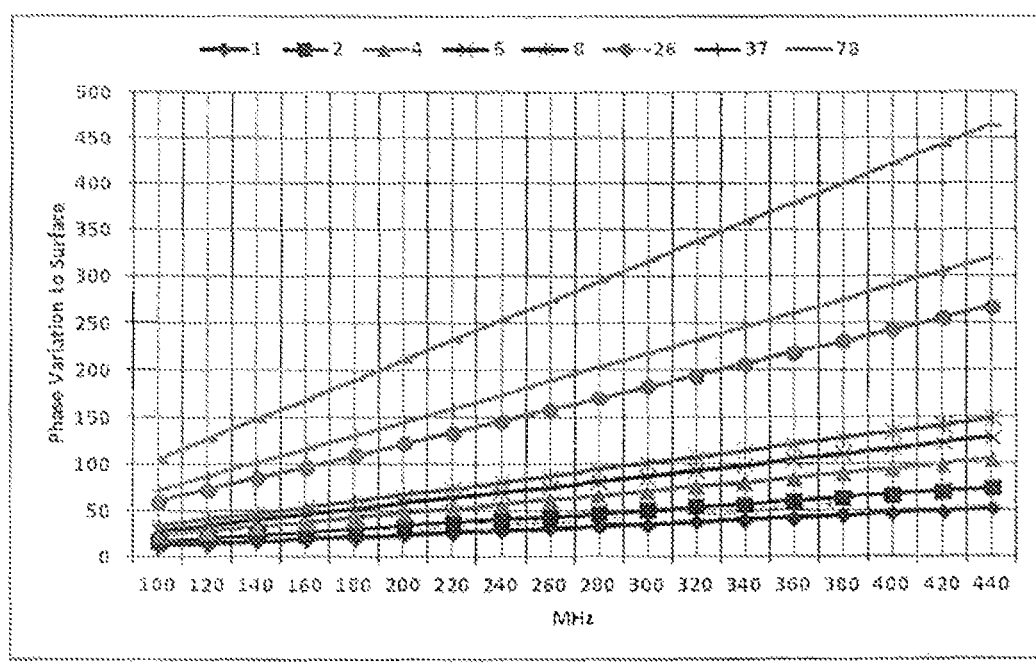

FIG. 7 is a graph showing how the phase difference between the A and C distances with respect to frequency and bolus media dielectric constant with the bolus having an outer diameter of 60 cm when signal path phase focusing is set on the radio frequency power channels. The vertical axis of the graph represents the phase difference at point 72 and the horizontal axis represents the frequency of the radio frequency signal from the antennas. Line 74 indicates the frequency difference with signal frequency when using a bolus media having a dielectric constant of 78. This is the value of dielectric constant of deionized water, the bolus media as used in the prior art. It can be seen that line 74 passes the phase difference of 135 at a signal frequency of about 160 MHz. Thus, when using a deionized water bolus of 60 cm outer diameter with a 28 cm body, the relationship determined by the inventors of having the difference in phase between distances A and C of less than 135 degrees is violated when using signal frequencies above about 160 MHz. Line 75 indicates the frequency difference when using a bolus media having a dielectric constant of 37. Ethylene glycol, which can be used as a bolus media has a dielectric constant of 37. When using a bolus media having a dielectric constant of 37, the signal frequency can be increased to about 230 MHz before the critical phase difference of 135 degrees is reached. Line 76 indicates the frequency difference when using a bolus media having a dielectric constant of 26. Propylene glycol, which also can be used as a bolus media, has a dielectric constant of 26. When using a bolus media having a dielectric constant of 26, the signal frequency can be increased to about 290 MHz before the critical phase difference of 135 degrees is reached. Line 77 indicates the frequency difference when using a bolus media having a dielectric constant of 8. Line 78 indicates the frequency difference when using a bolus media having a dielectric constant of 6. Line 79 indicates the frequency difference when using a bolus media having a dielectric constant of 4. Line 80 indicates the frequency difference when using a bolus media having a dielectric constant of 2. Line 81 indicates the frequency difference when using a bolus media having a dielectric constant of 1. It can be seen that by using a bolus media having a smaller dielectric constant than deionized water, such as ethylene glycol or propylene glycol, the frequency range for which the relationship of having the difference in phase between distances A and C of less than 135 degrees is extended. FIG. 8 is similar to FIG. 7 and shows the results when using a bolus having a smaller outside diameter of 44 cm. The graph line numbers between 74 and 81 are used in FIG. 8 to indicated dielectric constants of 78, 37, 26, 8, 6, 4, 2, and 1 respectively, similarly to FIG. 7. FIG. 9 is a similar plot showing the results when using a bolus having a still smaller outer diameter of 36 cm. FIGS. 7-9 show that for a particular bolus dielectric constant, as the bolus diameter gets smaller, the signal frequency maximum to meet the requirement of having the difference in phase between distances A and C of less than 135 degrees increases.

Figure 10:
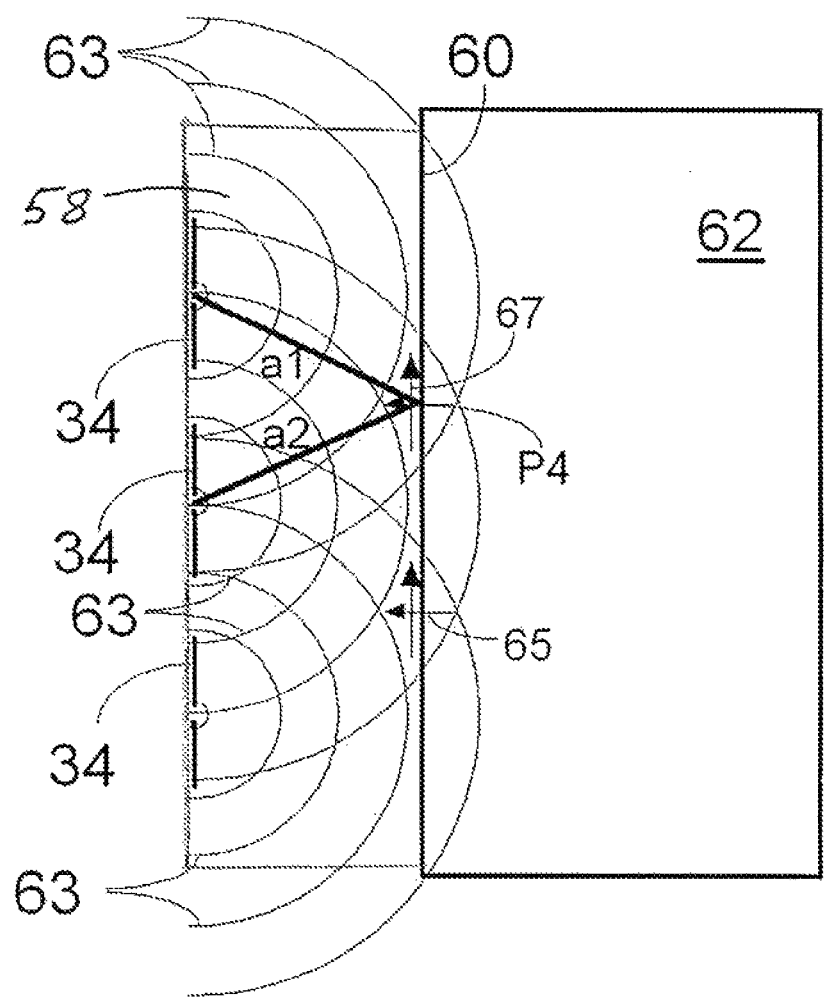
FIG. 10 represents the radio frequency signals radiated from the applicators stacked along the longitudinal axis of the tissue mass.

FIG. 10 represents a group 32 of the three stacked antennas 34 as shown in FIGS. 1-4, positioned along and spaced from the side surface, indicated as 60, of a tissue mass such as shown by 62 in FIG. 3 as representing a human torso containing the tissue to be heat treated therein. Such tissue mass will generally have an outer surface fat tissue layer surrounding the muscle tissue therein. The antennas 34 are located in a bolus 58, with the space between the antennas 34 and the tissue surface 60 being the bolus 58 as shown in FIG. 3. During operation of the system, each of the antennas 34 will radiate radio frequency signals, indicated as 63, of a particular frequency and phase toward the tissue mass 62. These signals will be superimposed along the surface 60 of the tissue and cause a horizontal electric field that is perpendicular to the tissue surface at the common point of intersection to the tissue surface fat layer. The horizontal electric field is indicated by arrow 65. The dominant direction of the electric field produced by the antennas is indicated by arrow 67. Surface fat tissue heating is strongly increased by such perpendicular electric fields. FIG. 10 shows equal length signal paths a1 from an end dipole antenna 34 and a2 from a central dipole antenna 34 which intersect at a point P4 along the tissue surface midway between the two antennas from which they emanate. As indicated, these signals will be superimposed at point P4 and cause a horizontal electric field indicated by arrow 65 that is perpendicular to the tissue surface at point P4. When the electric field radiated from these two antennas are at the same phase, there is a cancellation of the perpendicular field at this intersecting signal path location, P4, which will reduce heating of the fat tissue at that point. If however, the radiating phase of these two antennas is different, then the superimposition of the two signals forming the perpendicular electric field do not cancel but their respective powers will add to create a perpendicular electric field value which will cause fat tissue heating. If, for example, the radiating phase from the respective antennas for signal paths a1 and a2 is different by 90 degrees, such a phase setting will cause the radial E field 65 that is perpendicular to the tissue surface at point P4 to be at a 90 degree phase angle. Such a field may cause excessive fat heating. More than a 90 degrees difference is even worse for fat heating. Further as the phase difference exceeds 125 degrees, it becomes likely that there will be multiple central foci formed which is especially likely at the higher frequencies described such as 434 MHz. This is most critical and evident if the three phases are 180 degrees different in these longitudinal axis stacked dipoles, because there would clearly be an energy focus offset to the longitudinal axis on each side of the primary central focus. Therefore, in a stacked phased array design in a radio frequency annular phased antenna array hyperthermia system, two limitations should be met. In such a system the respective stacked antennas should not be spaced apart along the longitudinal axis of the tissue mass a distance that would result in a 3D focus phase difference that is more than 125 degrees. Also the actual separation distance of the longitudinal stacked antenna feed points should not exceed a distance that is more than a distance representing a 0.8 of the bolus media wavelength at the operating frequency of the system. This will avoid excessive heating displaced along the longitudinal axis from the primary focus center (desired heating zone). Also, the respective stacked antennas should not be located and operated so that the phase difference between signals from adjacent antennas at the point of intersection of equal length paths from the adjacent stacked antennas with the tissue surface, point P4, are greater than 125 degrees. This will moderate the potential for superficial fat tissue heating from the resulting radial E-fields at the bolus fat tissue interface. Note that the design of an antenna array spacing and operating frequency and bolus all relate to the needed phase between adjacent antennas to achieve the central focus as determined by signal path calculations.

The dielectric constant of the bolus media also sets a limit to the position and spacing of the long axis stacked antennas, i.e., the spacing between antenna rings, for a particular frequency and tissue size.

Figure 11:
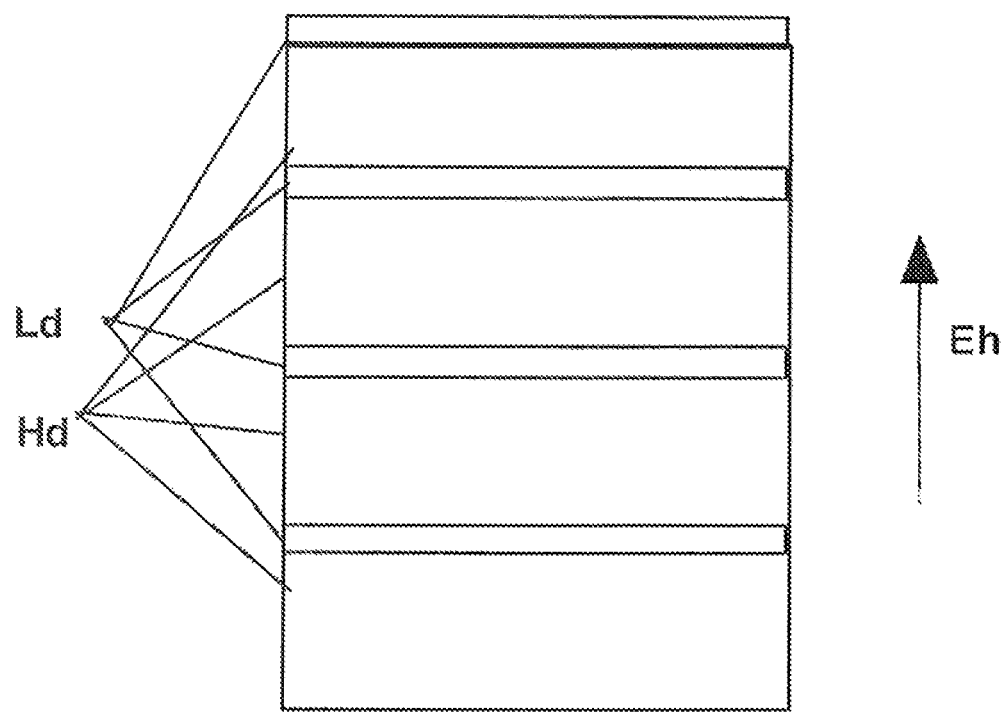
FIG. 11 shows an artificial dielectric that can be used with the invention.

As indicated above, the bolus media used can be critical in meeting the requirements set forth in this invention. The dielectric constant of the bolus media will determine the wavelength of a signal in the bolus media. If a bolus media having the desired dielectric constant and desired other properties is not available, an artificial dielectric media may be able to be constructed with a combination of high and low dielectric constant materials, such as with deionized water and plastic. FIG. 11 shows how an artificial dielectric can be made for radiating fields that are linear using high and low dielectric plate sections. The layered dielectrics of a low and high dielectric material can cause an effective artificial dielectric that has an effective dielectric constant between the dielectric constants of the two layered dielectrics. Such dielectric interface surfaces are to be primarily perpendicular to the dominant electric field.

When the electric field is dominantly perpendicular to dielectric plates of different dielectrics, the effective dielectric constant can be made to be a value between the dielectric constants of the two dielectrics. For the construction shown in FIG. 11, Ld is a plate or vane of low dielectric constant material, such as plastic or rubber, and Hd is a plate or vane of high dielectric constant material. Eh is the dominant electric field that is perpendicular to these plates or vanes. To apply this, the distance between the plates of the same kind must be less than a quarter of a wavelength of the media between the plates. The dielectric constant is determined by the equation:

$$e3 := \left[ \frac{e2 \cdot (t2 + t1)}{\left(e2 \cdot \frac{t1}{e1}\right) + t2} \right]$$

Where e1 is the Ld dielectric, e2 is the Hd dielectric, t1 is the Ld thickness, t2 is the
Hd thickness and e3 is the resultant equivalent dielectric of the combined media.

Rather than the LD or HD being a plate or vane of material, either could be a dielectric material receiving space or receiving chamber. For example, the HD in FIG. 11 could be a space between LD plates which receives a high dielectric constant material, such as deionized water, or a chamber which receives the deionized water. The LD material could be a plastic or rubber chamber filled or partially filled with air or with a low dielectric constant material. A bolus could be constructed for use between the applicators and the body tissue to be treated where the low dielectric constant material is flexible plastic or rubber sheet material secured in the bolus and having space between each sheet to hold deionized water as the high dielectric constant material. The plastic or rubber sheet material can also form chambers which can be filled with either high dielectric constant material or low dielectric constant material.

While dipole antennas have been described for the applicators in the illustrated embodiments described above, various other types of antennas can be used such as slot antennas, patch antennas, or any other standard radio frequency or microwave antenna. In addition, while antennas that dominantly provide a linear polarized electric field that is dominantly aligned with the central body axis will be used, other alignments and polarizations can be used. For example, various rotated antenna alignments as well as orthogonal antenna pairs can be used to provide for bending of the electric fields in the body target areas that might be useful for overcoming a shadowing effect that may occur from different dielectric structures such as deep bone, fat, or air regions near the target zone.

Figure 12:
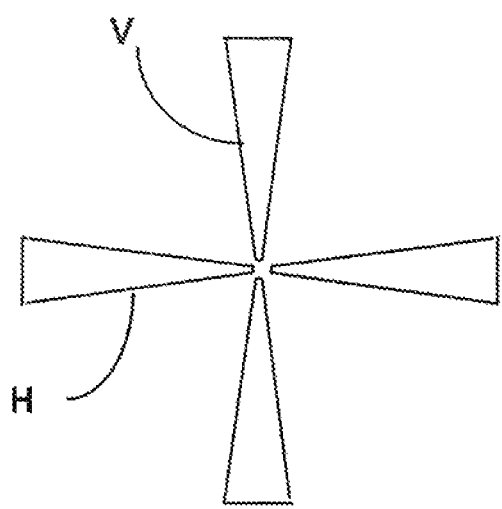
FIG. 12 shows an orthogonal dipole antenna pair usable with the invention.

FIG. 12 shows an orthogonal dipole antenna pair usable with the invention. This antenna includes two separate dipole antennas formed together as a pair. The dipole V radiates a dominant electric field polarization that is in the Z axis. The H dipole radiates a dominant electric field polarization that is in the X axis. Each dipole can be connected to a separate amplifier channel with its own power and phase control but operating at the same frequency. If there is no power on the dipole H the electric field is dominantly aligned along the Z axis in the dipole central zone as it radiates from the dipole. If there is no power on the dipole V the electric field is dominantly aligned along the X axis in the dipole central zone as it radiates from the dipole. If there is equal power on the dipoles V and H and the phase of V is the same as that of H, the radiated electric field is dominantly linear and aligned at a 45 degree angle to the X and Z axes. Each dipole can have a different relative phase to the other dipole. As the relative phases are changed and the relative power to each are changed, the polarization can change from various linear polarized angles to elliptical or circular polarization.

Figure 13:
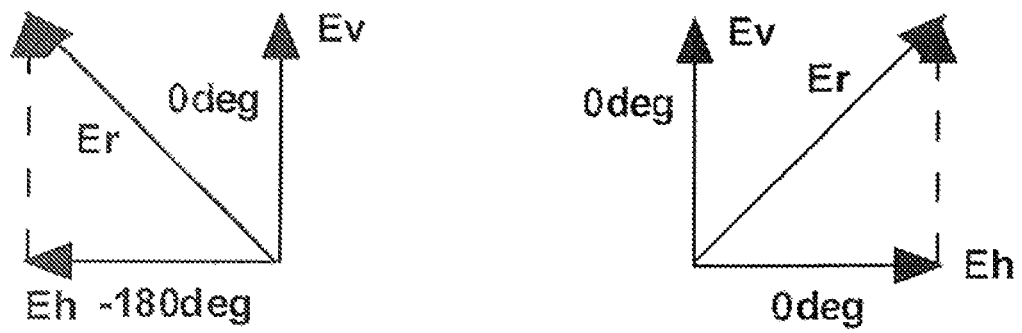
FIG. 13 shows how the electric field in the vertical and horizontal axis can be altered in the relative phase to change the resulting electric field.

FIG. 13 shows how the electric field in the vertical and horizontal axis can be altered in the relative phase to change the resulting electric field to be tilted by + or −45 degrees using either a 0 or 180 phase difference.

Er shows how linear electric field polarization can be radiated by changing the relative phase between the two orthogonal dipoles. If there is equal power on the dipoles V and H and the phase of V is 90 degrees different than that of H, the radiated electric field is dominantly circularly polarized. Circularly polarization is when the pointing direction of the radiating electric field rotates in the plane that is perpendicular to the radiating direction as it travels away from the source. The relative phase between the H and V dipoles can change from right hand to left hand circular polarization as well as creating elliptical polarization radiated fields.

The phased array of such orthogonal dipole pairs can results in significant differences in the tissue heating pattern generated. The ability to rotate the polarization angle can also alter the electric fields between various tissues of the body. This can be used to improve heating in areas that may be otherwise heated less. An example of this is the rectal area that is below the bending spinal bone area of the pelvis that is known to have a zone less heated adjacent to the bone due to the dominance of a perpendicular electric field at the tissue to bone interface.

Figure 14:
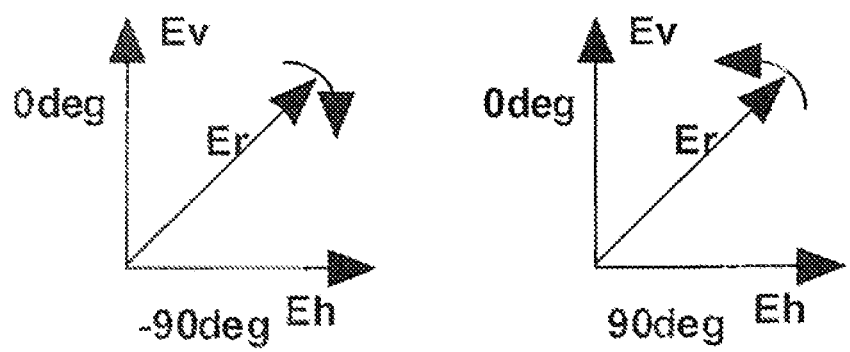
FIG. 14 shows how a change in relative phase of + or −90 degrees can cause a right hand or left hand circularly polarized radiated electric field

FIG. 14 shows how a change in relative phase of + or −90 degrees can cause a right hand or left hand circularly polarized radiated electric field. Er shows how circularly polarized electric fields can be radiated by changing the relative phase between the two orthogonal dipoles. When this capability is part of a phased array system, it provides additional and unique capability to control the heating fields to better heat tissues of the body. This is particularly the case if there is some tissue target zones that may be heated less due to the dominant electric field polarization in relation to neighboring tissues that are of a different dielectric.

FIGS. 15-51 show the results, using a COMSOL based modeling program developed by the inventors, of the SAR (specific absorption rate) of the radio frequency energy from the radio frequency signal, which is indicative of the heating, in a tissue model representing the human torso within the bolus of a radio frequency annular array hyperthermia system operated using different parameters of frequency, bolus size, bolus dielectric values, and number of antennas. The tissue model is modeled as having a one cm fat layer (low water content tissue) surrounding a cylinder of muscle tissue (high water content tissue). When shown as a round cylinder, the cylinder has a diameter of 28 cm. When shown as an elliptically shaped cylinder with elongated cross section such as shown in FIG. 3, the cylinder has a major axis of 35.5 cm and a minor axis of 23 cm. As indicated, the goal of the invention is to provide a heating zone within the torso of a human body (the tissue model represents the human torso) that is approximately 8 cm in diameter or less. This means that all points within a heating zone with a diameter of 8 cm, corresponding to a volume of 270 cubic centimeters of tissue, the relative SAR (Specific Absorption Rate, or absorbed power per unit mass) would be within 50% of the maximum SAR in the high water content tissue model portion. The COMSOL modeling program provides color patterns within a desired tissue area with different colors representing the SAR at various locations within the tissue area. FIGS. 15-51 are representations of such color patterns showing the outlines of the relative percentage specific SAR areas in the tissue model. These lines are referred to as the relative percentage power density or SAR (specific absorption rate) contour lines. Generally in these FIGS., the large circle indicated by reference number 90 in each FIG. represents the outer dielectric bolus boundary (formed by the clear plastic or dielectric cylinder 54 in FIGS. 3, 5, and 6) where there is air outside that. The antennas 34 are shown just inside the bolus boundary 90. The first circle inside the bolus, indicated by reference number 91 in each drawing, represents the outer surface of the tissue model, which is the outside surface of the fat layer. The next circle inward, indicated by reference number 92 in each drawing, represents the inner surface of the tissue fat layer and outer surface of the high water content tissue of the tissue model, sometimes referred to with reference number 93. This can be modeled as either a saline simulation or a muscle tissue simulation. The muscle tissue simulation takes into account that the tissue dielectric value will vary with frequency of the radio frequency signal, the dielectric value of muscle being less with higher frequency signals. The dielectric value of saline will substantially equal the tissue dielectric value for signal wavelengths between about 80 and 100 MHZ. Saline is a generally used model of tissue in the prior art so saline has been used in some examples modeled to provide a more direct comparison with prior art studies. The additional lines in the Figs are the SAR contour lines with the percentage numbers between or on such lines indicating the relative SAR within such lines. Generally a 70% contour line, a 50% contour line, and a 20% contour line are shown. Other contour lines are shown in some of the FIGS. The tissue maximum for each FIG. has been adjusted to 100% for the data display shown.

Figure 15:
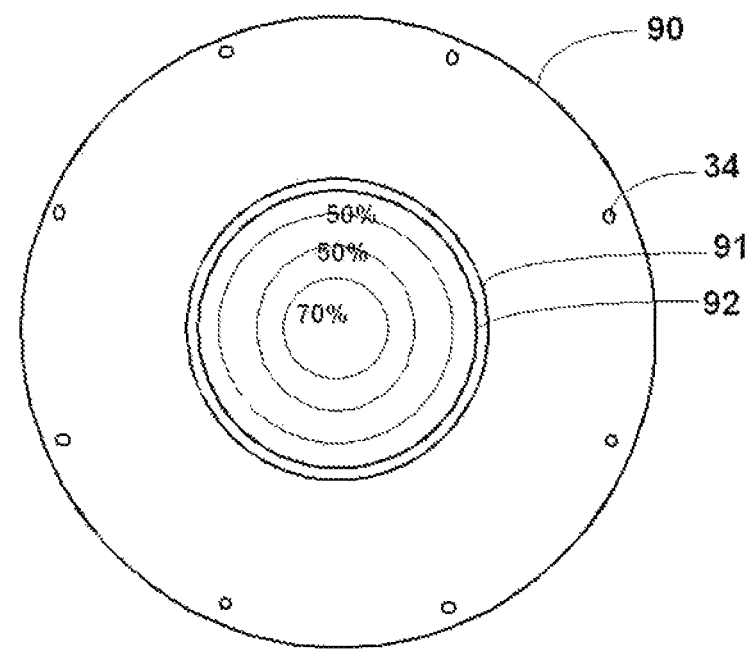
FIGS. 15-51 are simulations of heating patterns produced by an annular phased array hyperthermia system operated with various configurations and at various operating parameters.
Figure 16:
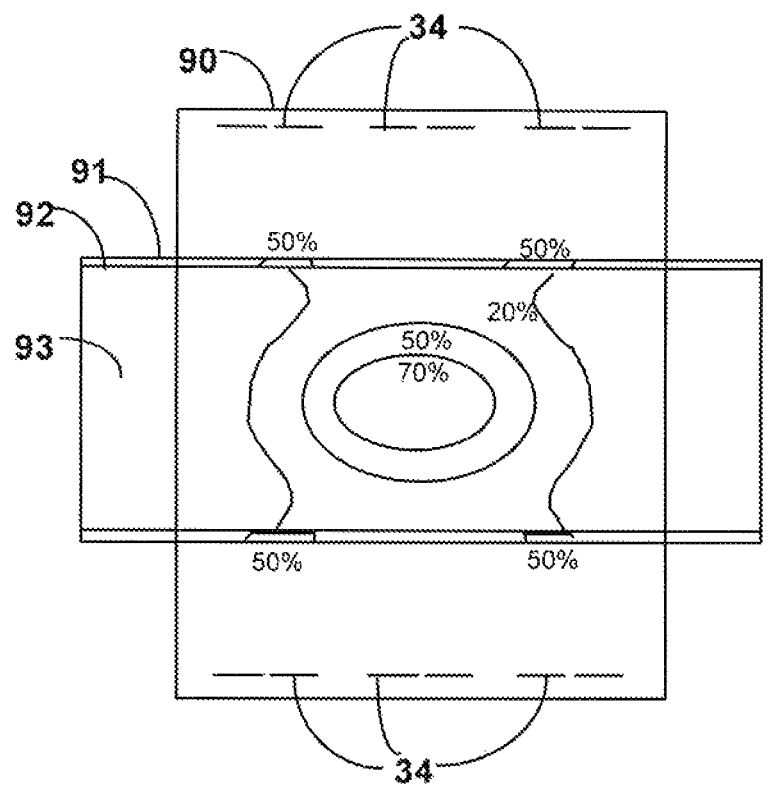

FIGS. 15 and 16 show the result of operation of a system according to the prior art at a frequency of 100 MHz and with a deionized water filled bolus having an outer diameter of 60 cm and extending for a length of 48 cm in the axial direction along the outside of and surrounding the tissue model 93 as shown in FIG. 16. The tissue model is a saline model. FIG. 15 is a horizontal section through the center of the tissue model and shows a circular center heating zone within the 50% contour line. The volume shown within the 50% contour line is the 50% SAR volume determined by measuring the three orthogonal diameters of the central focus zone. The tissue model is shown surrounded by the bolus and eight antennas. FIG. 16 is a section along the central axis of the phantom showing opposite antennas 34 of the three rings of antennas (similar to the arrangement in FIGS. 2 and 4) which extend axially along opposite sides of the width of the tissue model 93. FIG. 16 shows that the heating zone generated by the system is elongated along the longitudinal axis of the tissue model. FIGS. 15 and 16 show the large central energy focus for the power deposition (the heating zone) from the array of dipole antennas using the prior art 100 MHz signal frequency. The volume of tissue in the 50% SAR heating zone is 1957 cc. This is much larger than an eight cc diameter tumor so results in heating much of the normal tissues surrounding the tumor. Therefore, the temperature within the heating zone has to be limited to the tolerance levels of normal tissue exposure. This limits the therapeutic benefit that would otherwise be possible. FIG. 16 also shows the creation of two hot spots with 50% SAR in the fat layer of the tissue model spaced along the tissue model axis a distance to place then about even with the ends of the central 50% SAR heating zone.

Figure 17:
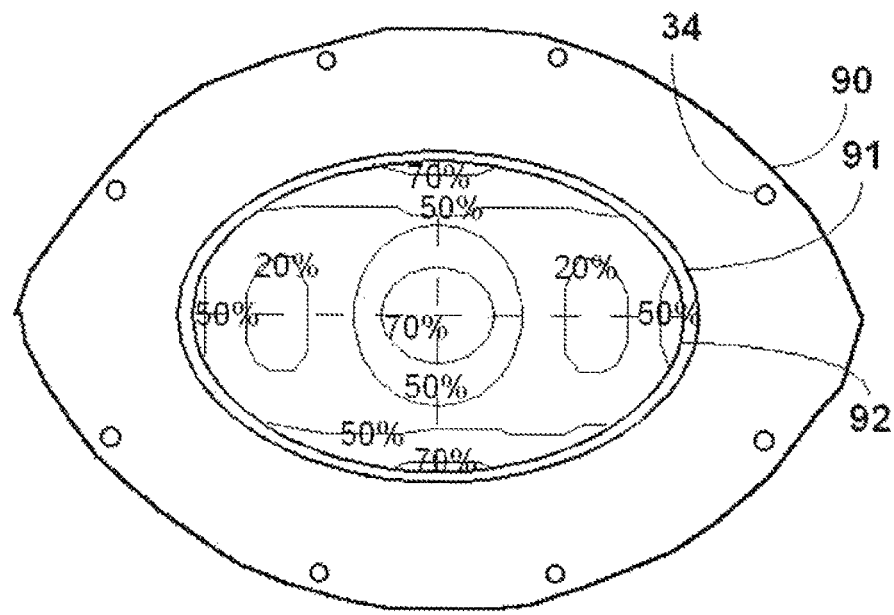
Figure 18:
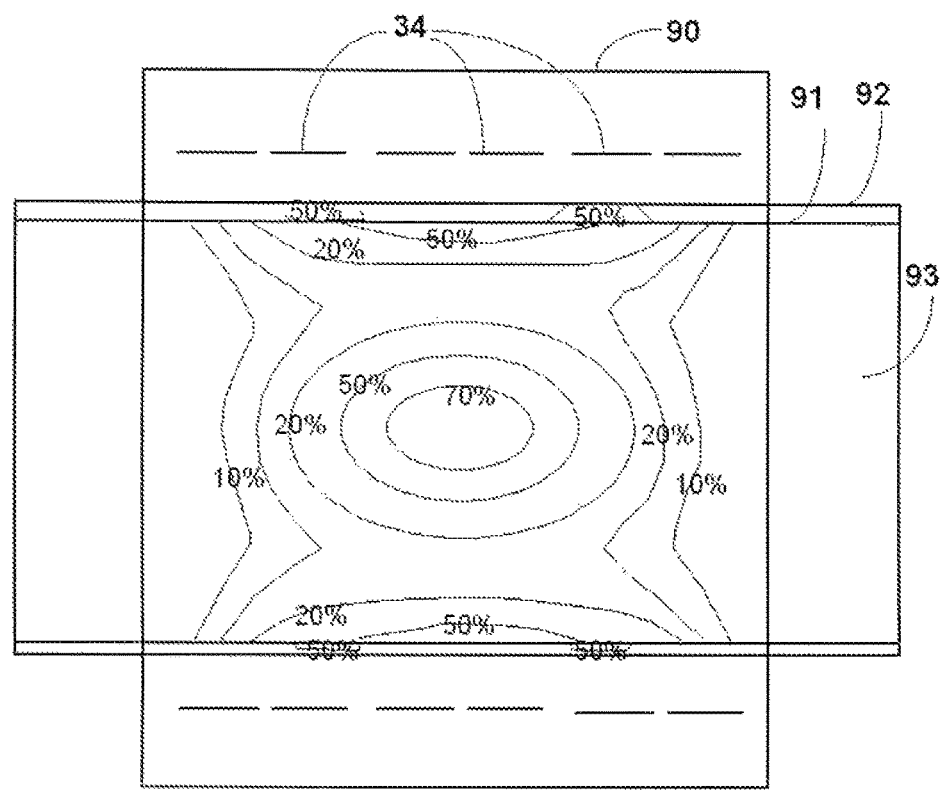

FIGS. 17 and 18 show the result of operation of a system having an elongated bolus and antenna array as in the prior art BSD 1000 Sigma Eye hyperthermia system and operating at a slightly higher than prior art frequency of 140 MHz with a deionized water filled bolus having an outer major diameter of 54 cm and a minor diameter of 37 cm. The bolus extends for a length of 48 cm in the axial direction along the outside of and surrounding the tissue model 93. This bolus shape is made by using a plastic cylinder that has a diameter of 58.42 cm that is cut along the long axis to form two sections that are bonded together making the minor inner bolus diameter size of 37 cm and two plastic cylinders forming the long sides of the bolus, each side being an arc with a 29.21 cm diameter of a length to form the bolus major diameter of 54 cm. The tissue model is an elliptical saline model having a major diameter of 35.5 cm and a minor diameter of 23 cm. FIG. 17 is a horizontal section through the center of the tissue model and shows a large circular center heating zone similar to that of FIG. 15 within the 50% SAR contour line. Again, this is a larger than desired central heating zone with a volume of 1475 cm. In addition to the central heating zone within the 50% SAR contour line, FIG. 17 also shows high heating zones above 50% SAR, and up to 70% SAR, along the outside edges of the elongated tissue model at the interface of the muscle and fat tissue. It also shows some fat layer heating similar to that of FIG. 15. FIG. 18 is a section along the central axis of the tissue model and also shows the hot spots along the edges of the tissue model. FIG. 18 also shows an elongate heating zone along the longitudinal axis of the tissue model. While FIGS. 17 and 18 show some undesirable hot spots away from the central heating zone and these could damage the normal tissue in these hot spot zones, this is a similar pattern to that created using 100 MHz signals (not shown). Therefore, with this arrangement, as with the arrangement of FIGS. 15 and 16, the temperature within the heating zones has to be limited to the tolerance levels of normal tissue exposure.

Figure 19:
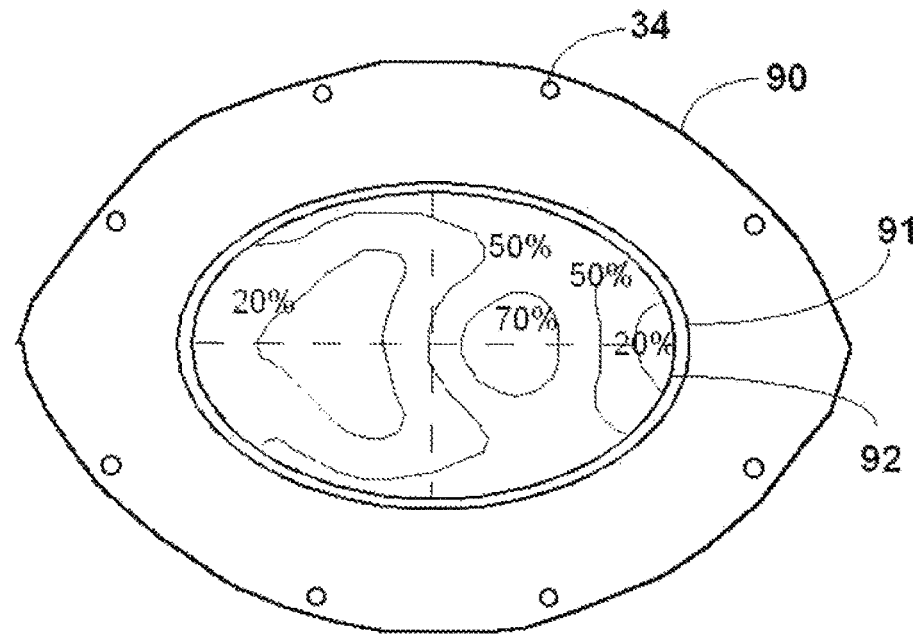
Figure 20:
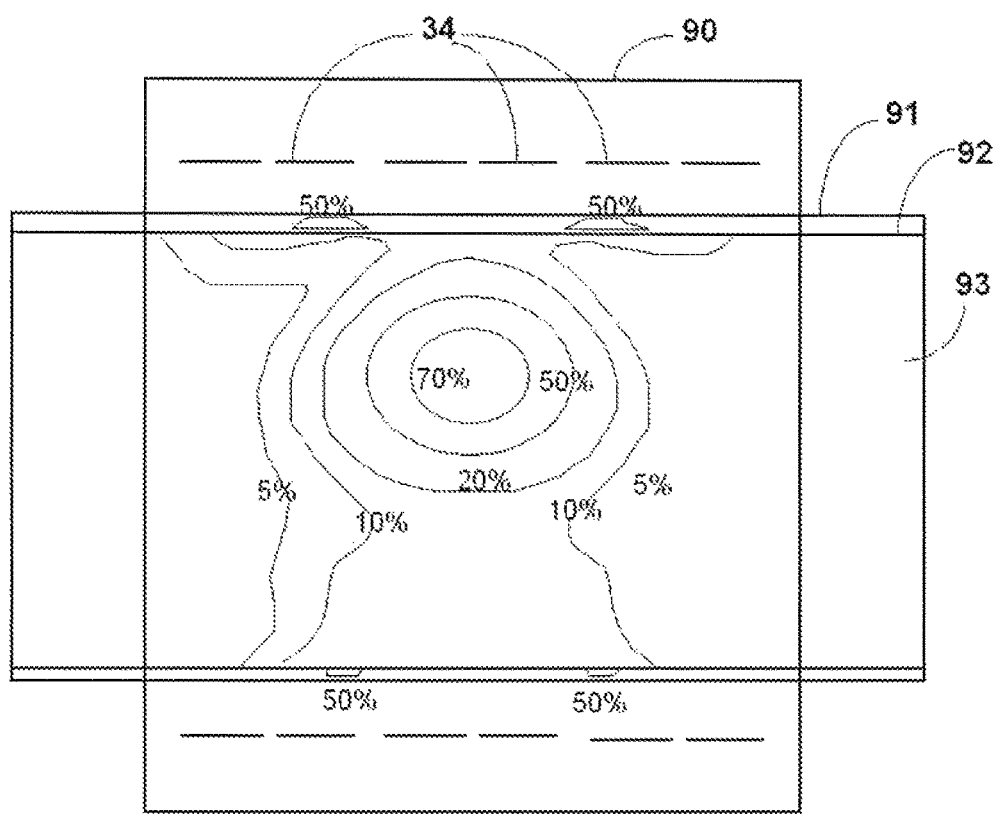

FIGS. 19 and 20 show the result of operation of the system of FIGS. 17 and 18 having an elongate bolus and antenna array as in the prior art BSD 1000 Sigma Eye hyperthermia system and operating at a frequency of 140 MHz with a deionized water filled bolus having an outer major diameter of 54 cm and a minor diameter of 37 cm. The bolus extends for a length of 48 cm in the axial direction along the outside of and surrounding the tissue model 93. The tissue model is an elliptical muscle tissue model having a major diameter of 35.5 cm and a minor diameter of 23 cm. The difference in operation and the resulting heating patterns from those shown in FIGS. 17 and 18 is that the phases of the radio frequency signals from the respective antennas have been adjusted, in prior art manner, to steer the heating zone to a position wherein the heating zone is offset to the right in FIG. 19 from the center minor axis by four cm. FIG. 19 is a horizontal section through the center of the tissue model and shows the offset. While a substantially circular 70% SAR heating zone is generated centrally in the tissue model, the 50% SAR heating zone, while offset to the right as desired, extends completely from side to side through the tissue model and along opposite sides of the muscle fat interface. In order to reduce the heating along the tissue fat interface, the power of the signal radiated from the opposite two side antennas, i.e., the two antennas at the left side for each of the three antenna rings and the two antennas at the right side for each of the three antenna rings in FIG. 19, have been reduced to half power. Again, this provides a heating zone much larger than desired and extends through a large area of normal tissue. FIG. 20 is a section along the central axis of the tissue model and shows the 70% and 50% SAR heating zones. Again, since the heating zone includes a substantial amount of normal tissue, the temperature within the heating zones has to be limited to the tolerance levels of normal tissue exposure.

FIGS. 15 through 20 show the heating to be expected using a prior art radio frequency phased array hyperthermia system operated using prior art frequencies up to 120 MHz (140 MHz produces similar results as 100 MHz and 120 MHz would) with a deionized water bolus, and three rings of eight antennas around the outer edge of the bolus. As shown, the heating zones produced are relatively large and include substantial amounts of normal tissue in the heating zone along with the tumor tissue to be treated. In order to produce smaller heating zones, higher frequencies for the radio frequency signals must be used. FIGS. 21-51 show the result of operation of a radio frequency annular array hyperthermia system having a bolus surrounding the tissue mass containing the tissue to be treated and an antenna array operating at a higher than prior art system frequency, such as 250 MHz. At these higher frequencies, it is necessary to operate the system using the new device parameters and methods of the invention in order to produce satisfactory heating zones within the relatively large tissue masses as represented by a human torso.

Figure 21:
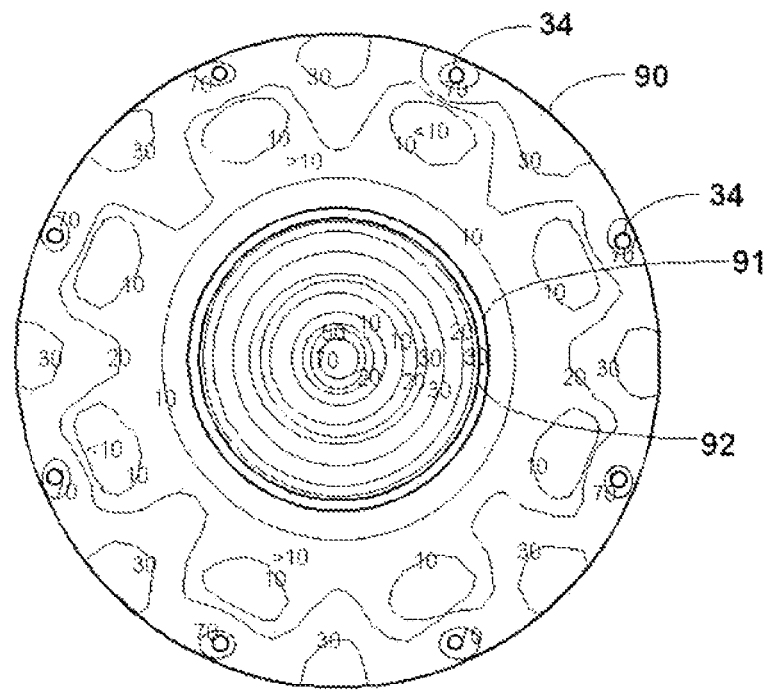
Figure 22:
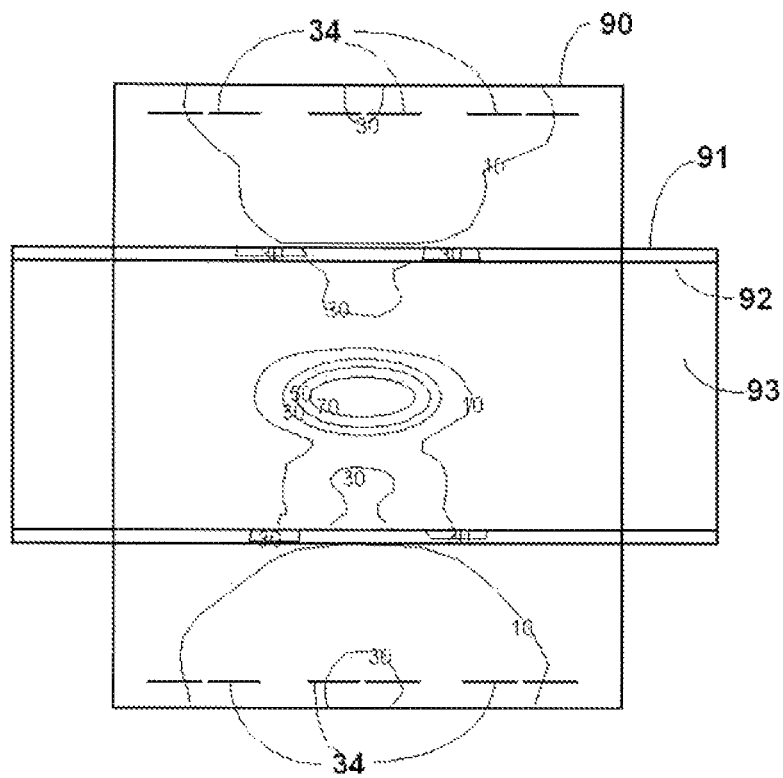

FIGS. 21 and 22 show the result of operation of a radio frequency annular array hyperthermia system having a circular bolus and antenna array operating at a higher than prior art system frequency of 250 MHz. As in the system for generating the heating patterns of FIGS. 15 and 16, the bolus has an outer diameter of 60 cm and extends for a length of 48 cm in the axial direction along the outside of and surrounding the tissue model 93. However, in the system for generating the heating patterns of FIGS. 21 and 22, the bolus is filled with a fluid having a dielectric constant substantially less than the dielectric constant of 78 for deionized water as used in the prior art. For FIGS. 21 and 22, the bolus is filled with propylene glycol having a dielectric constant of 26. FIG. 21 is a horizontal section through the center of the tissue model and shows a small circular center heating zone within the 50% contour line. The volume of tissue in the 50% heating zone is only 206 cc. This is the desired result of producing a relatively small heating zone in a relatively large tissue mass. FIG. 21 shows hot spots around the antennas in the bolus, but these are in the bolus, not in the tissue. Therefore they do not cause tissue heating. Any heating of the bolus fluid caused by these hot spots can be dealt with by circulating and cooling the bolus fluid, if necessary. FIG. 22 shows this heating zone has an elongate shape along the longitudinal axis of the tissue model.

Figure 23:
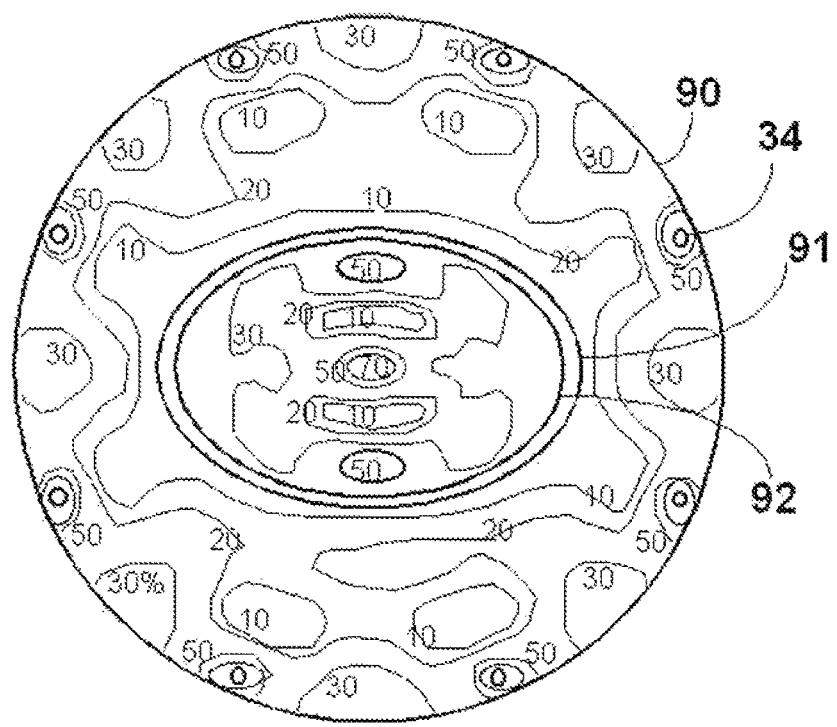
Figure 24:
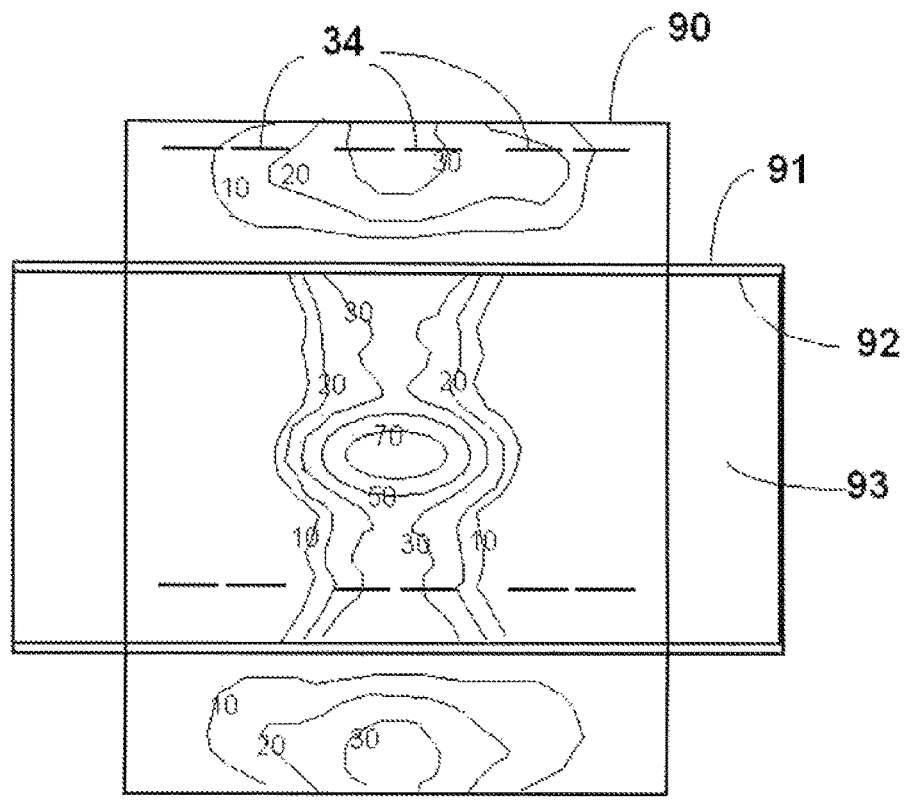
Figure 25:
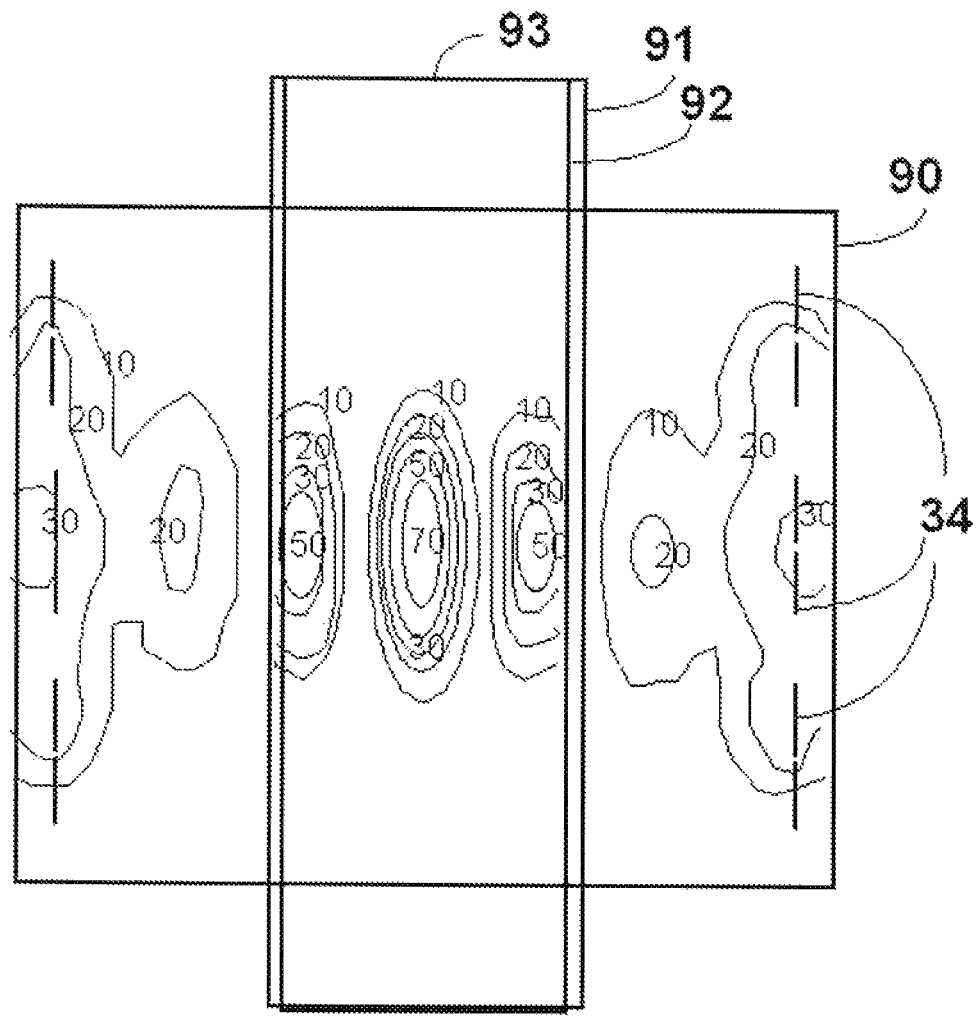

FIGS. 23, 24, and 25 show the result of operation of a system having a circular bolus and antenna array operating at a frequency of 250 MHz with a propylene glycol filled bolus having an outer diameter of 60 cm and a length of 48 cm in the axial direction along the outside of and surrounding the tissue model 93. The tissue model is an elliptical saline model having a major diameter of 35.5 cm and a minor diameter of 23 cm. FIG. 23 is a horizontal section through the center of the tissue model and shows a small circular center heating zone within the 50% SAR contour line. The volume of tissue in the central 50% SAR heating zone is only 176 cc. FIGS. 23 and 25 shows two separate hot spots within 50% SAR contours spaced from the center heating zone toward the interface of the tissue with the inside of the fat layer. These could cause unwanted heating away from the central heating zone. FIG. 23 also shows hot spots around the antennas in the bolus, but these are in the bolus, not in the tissue. Therefore they do not cause tissue heating. FIGS. 24 and 25 show the heating zones have an elongate shape along the longitudinal axis of the tissue model.

Figure 26:
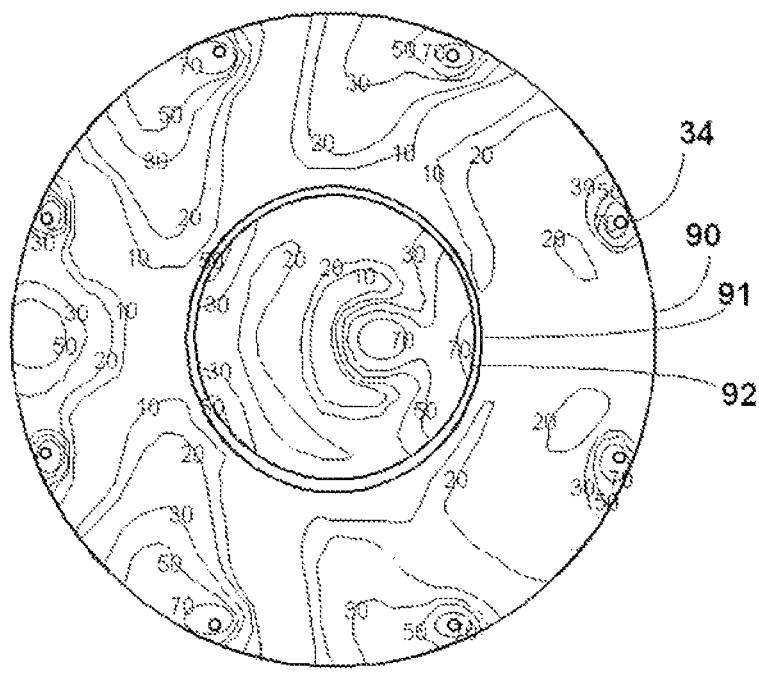
Figure 27:
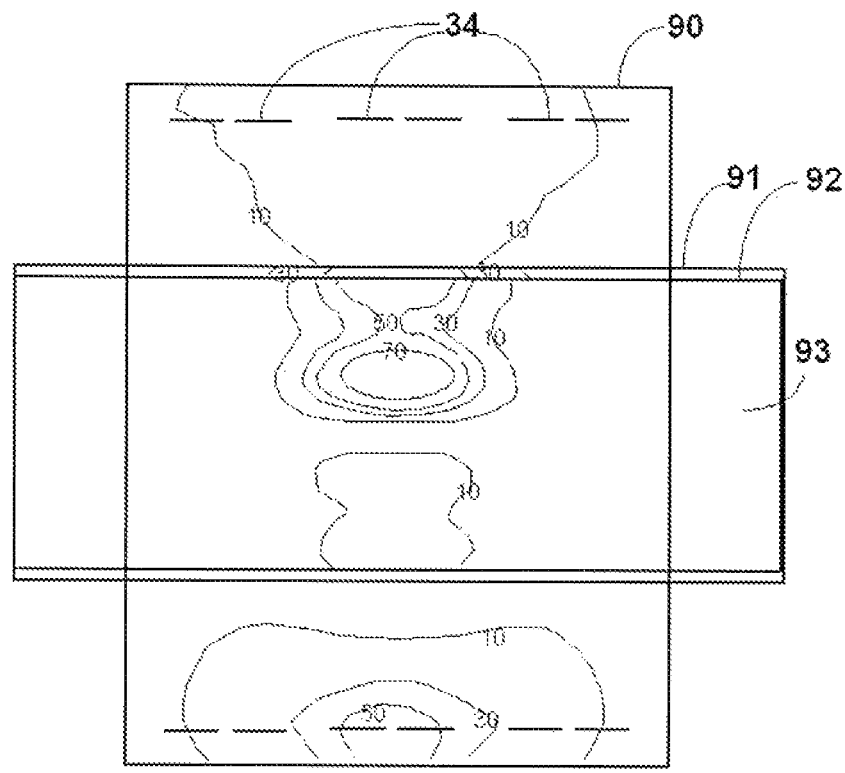

FIGS. 26 and 27 show the result of operation of a system similar to that of FIGS. 21 and 22 having a circular bolus and antenna array operating at a frequency of 250 MHz with a propylene glycol filled bolus having an outer diameter of 60 cm. The bolus extends for a length of 48 cm in the axial direction along the outside of and surrounding the tissue model 93. The tissue model is a circular cylindrical saline model for better comparison with the model of FIGS. 15 and 16. The difference in operation and the resulting heating patterns from those shown in FIGS. 21 and 22 is that the phases of the radio frequency signals from the respective antennas have been adjusted to steer the heating zone to a position wherein the heating zone is offset to the right in FIG. 26 from the center of the tissue model by four cm. FIG. 26 is a horizontal section through the center of the tissue model and shows the offset. A substantially circular 70% SAR heating zone is generated along the axis of the tissue model offset to the right of the center of the tissue model, and the 50% SAR heating zone is also offset from the radial center and extends all of the way to and through the fat layer at the right of the tissue model. In this condition, the volume of the 50% SAR heating area is 296 cc. This again is the desired relatively small heating zone. Two very small hot spots are shown at the tissue fat layer interface at the left side of the tissue model in FIG. 26, and hot spots are shown around the antennas in the bolus.

Figure 28:
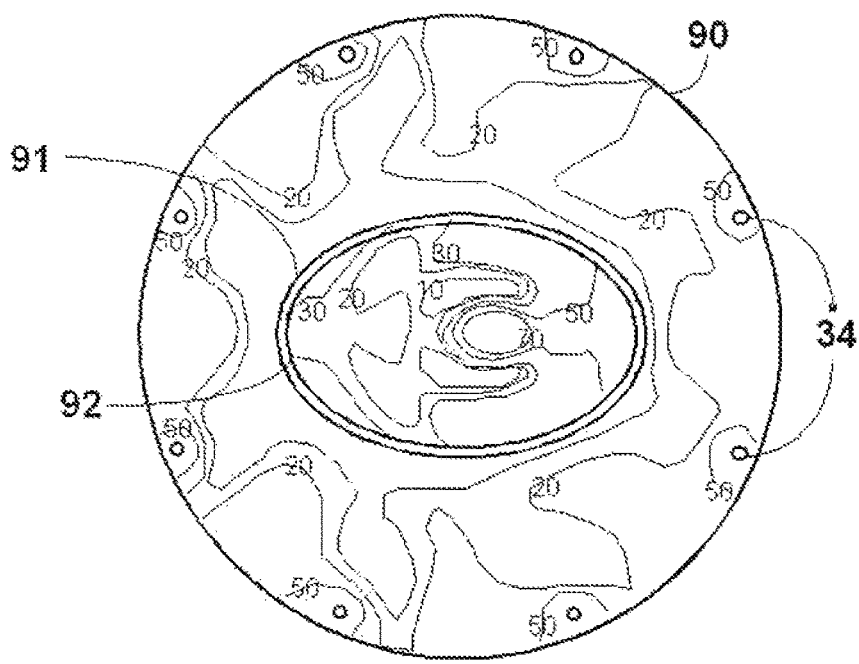
Figure 29:
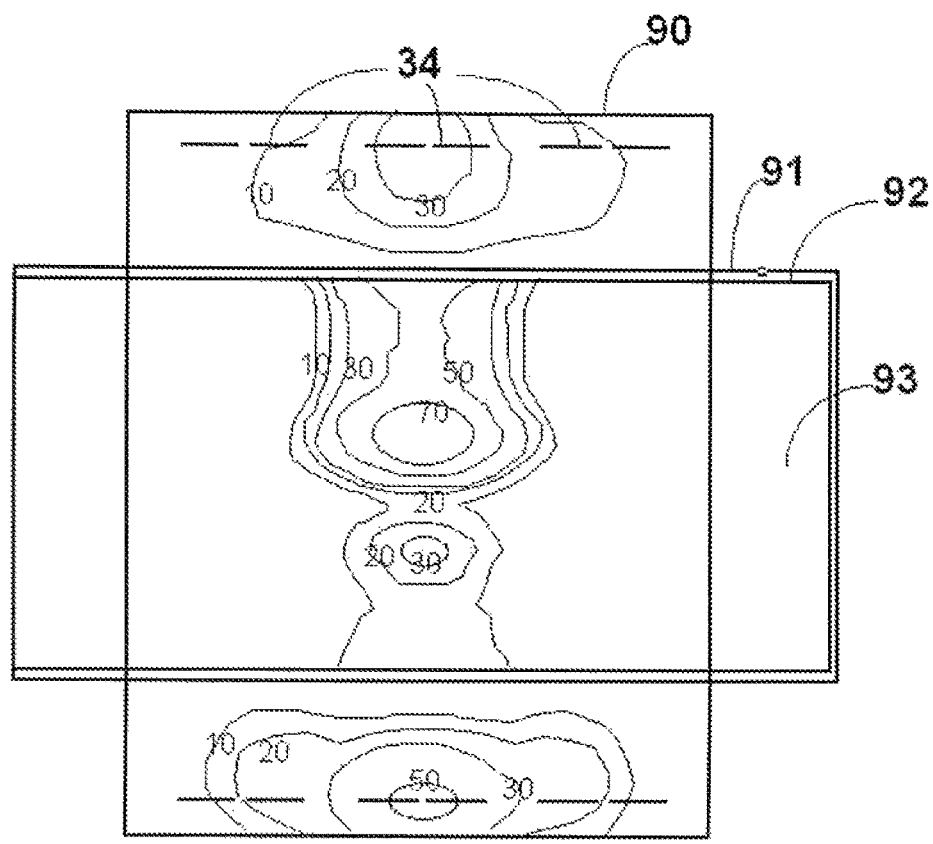

FIGS. 28 and 29 show the result of operation of a system similar to that of FIGS. 24 and 25 having a circular bolus and antenna array operating at a frequency of 250 MHz with a propylene glycol filled bolus having an outer diameter of 60 cm. The bolus extends for a length of 48 cm in the axial direction along the outside of and surrounding the tissue model 93. Rather than a circular cylindrical saline model, the tissue model for FIGS. 28 and 29 is an elliptical cross section cylindrical muscle tissue model having a major diameter of 35.5 cm and a minor diameter of 23 cm. As for FIGS. 26 and 27, the phases of the radio frequency signals from the respective antennas have been adjusted to steer the heating zone to a position wherein the heating zone is offset to the right in FIG. 28 from the center of the tissue model by four cm. FIG. 28 is a horizontal section through the center of the tissue model and shows the offset. An elongate 70% SAR heating zone is generated along the axis of the tissue model offset to the right of the center of the tissue model, and the 50% SAR heating zone is also offset from the radial center and extends all of the way to the fat layer at the right of the tissue model. The 50% SAR zone is narrower than that of FIG. 26 as it extends to the fat layer. In this condition, the volume of the 50% SAR heating volume is 275 cc in the primary focal zone but extends to the surface making a total volume of 480 cc. This again is the desired relatively small heating zone relative to the state of the art, but has increased spread to the surface increasing the volume beyond the desired goal. With this configuration of the tissue model, there are no small hot spots at the tissue fat layer interface at the left side of the tissue model in FIG. 28, but some lesser hot spots axially of the centered 70% SAR heating zone. There are also hot spots shown around the antennas in the bolus.

FIGS. 30-39 show unsatisfactory heating patterns produced when merely increasing the signal frequency of the radio frequency signals directed from the antenna array to the tissue model using the prior art arrangement of a deionized water bolus and arrangement of antennas therein, similar to the systems used for the heating patterns of FIGS. 15-21, or when making some adjustments, such as to the bolus, but where the recommended conditions are still not met.

Figure 30:
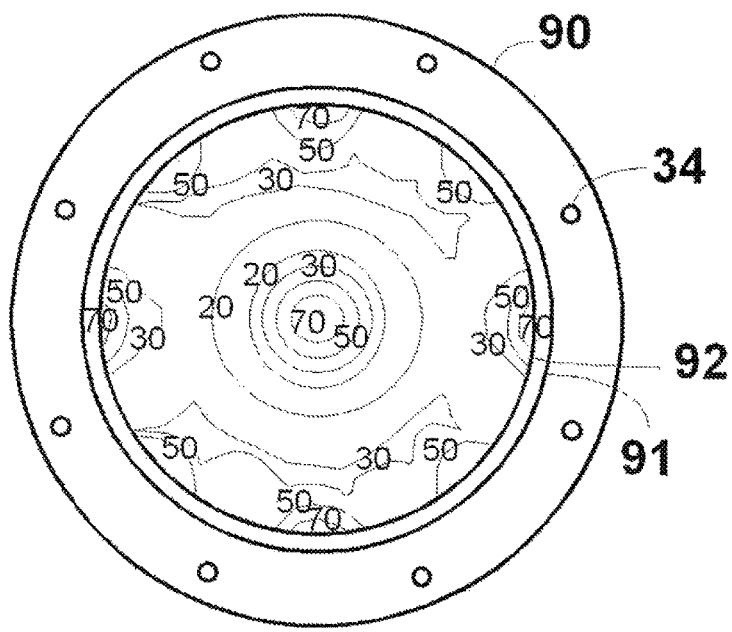
Figure 31:
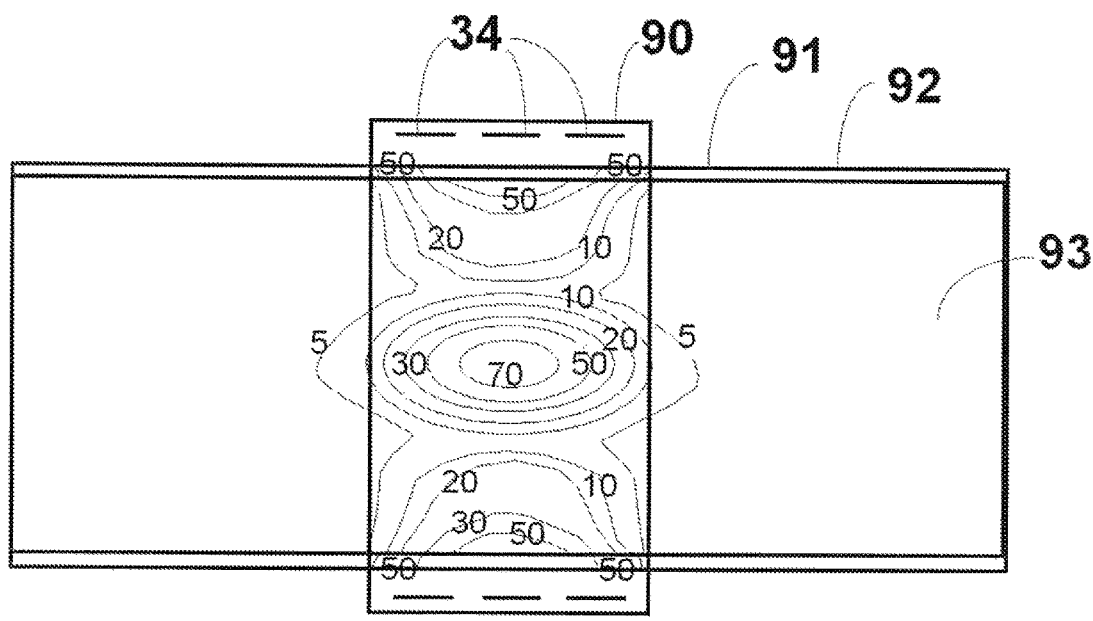

FIGS. 30 and 31 show the result of operation of a system according to the prior art but increasing the frequency of the signal to 250 MHz, well above the prior art maximum frequency of 120 MHz. The prior art system includes a deionized water filled bolus having an outer diameter for the purposes of FIGS. 30 and 31 of 36 cm. For purposes of illustration, the system modeled to generate the heating diagram of FIGS. 30 and 31 has three antenna rings with shorter antennas so the length of the bolus is modeled with a length of 19 cm in the axial direction along the outside of and surrounding the tissue model 93 as shown in FIG. 31. The tissue model is a saline model. FIG. 30 is a horizontal section through the center of the tissue model and shows a circular center heating zone within the 50% contour line having a volume of 138 cc. FIG. 31 is a section along the central axis of the tissue model showing that the heating zone generated by the system is elongated along the longitudinal axis of the tissue model. FIGS. 15 and 16 show that the higher frequency signal has provided a smaller central heating zone as desired and expected. However, significant hot spots occur between each of the antennas along the tissue fat layer interface which will result in heating of a significant volume of normal tissue at these spots. If the phase is determined for the A and C distances in the bolus as described for FIG. 6, and the phase difference calculated, it will be seen that the phase difference for the configuration of FIGS. 30 and 31 is 265 degrees. As indicated above, the inventors have determined that for satisfactory heat zone generation and distribution in the tissue, such phase difference should not exceed 135 degrees. This criteria has not been met in this case leading to poor heat pattern steering and superficial unwanted hot spots. The heating pattern generated is unsatisfactory due to the significant additional surface hotspots.

Figure 32:
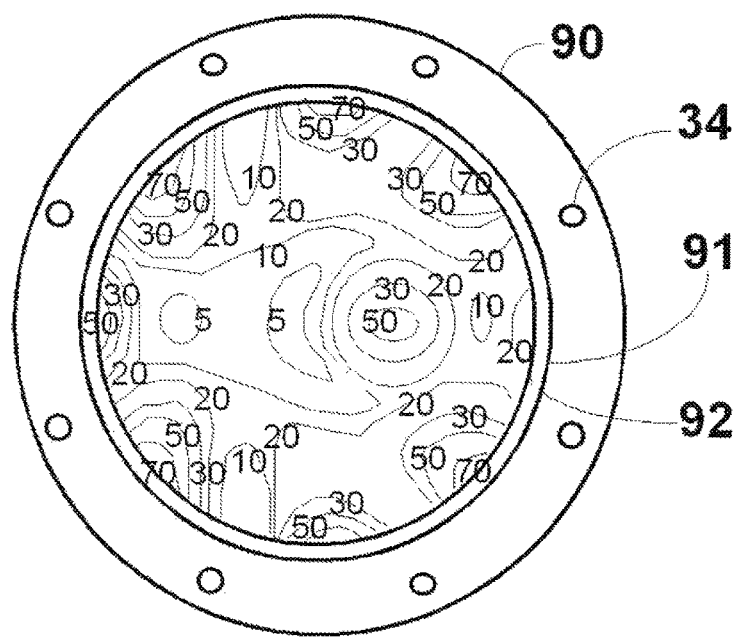
Figure 33:
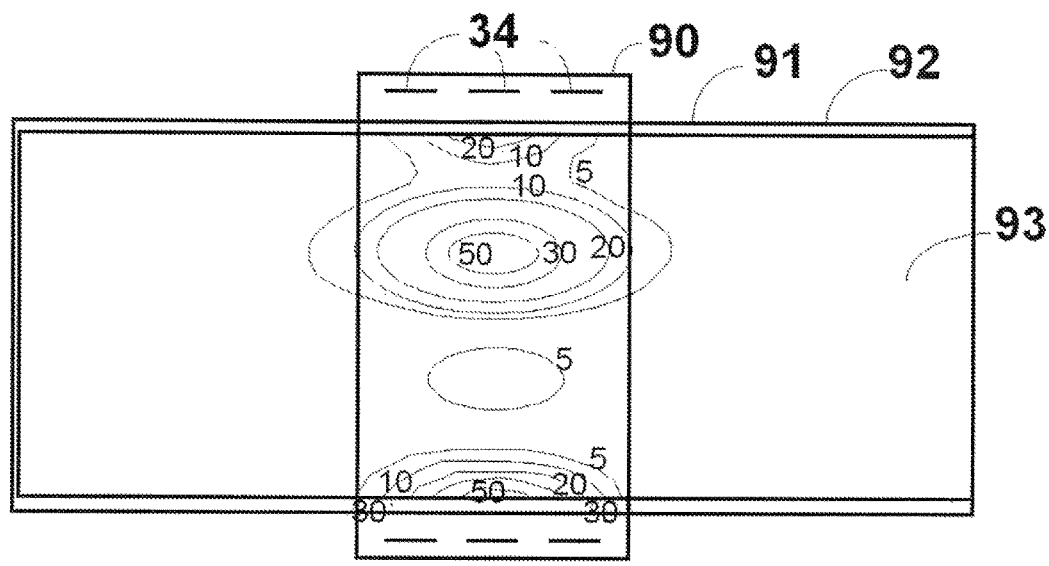

FIGS. 32 and 33 show the result of operation of the system used for generating FIGS. 30 and 31 using a frequency of 250 MHz and having an circular cross section bolus having an outer diameter of 36 cm. and three antenna rings with the shorter antennas so the length of the bolus is reduced to 19 cm in the axial direction along the outside of and surrounding the tissue model 93 as shown in FIG. 33. The difference in operation and the resulting heating patterns from those shown in FIGS. 30 and 31 is that the phases of the radio frequency signals from the respective antennas have been adjusted to steer the heating zone to a position wherein the heating zone is offset to the right in FIG. 19 from the center of the tissue model by four cm. FIG. 32 is a horizontal section through the center of the tissue model and shows the offset. While a substantially circular 50% SAR heating zone is generated centrally in the tissue model offset to the right as desired, the SAR within this central 50% SAR heating zone does not include SARs greater than 50%. The high SAR within 50% contours in FIGS. 32 and 33 occur in hot spots between each of the antennas along the tissue fat layer interface. This will result in substantial heating of these hot spots with little or no heating in the central 50% heating zone. This is a completely unsatisfactory heating pattern and shows that phase steering is not possible with this configuration. The calculation for the A and C distances in the bolus as described for FIG. 6, and the phase difference calculated, will be the same as for the configuration of FIGS. 30 and 31, and will show a phase difference of 265 degrees. The criteria that such phase difference should not exceed 135 degrees is not met. This heating pattern is unsatisfactory due to the lack of a significant heating zone for the tissue to be heated with the significant heating zones being located around the surface of the tissue mass.

Figure 34:
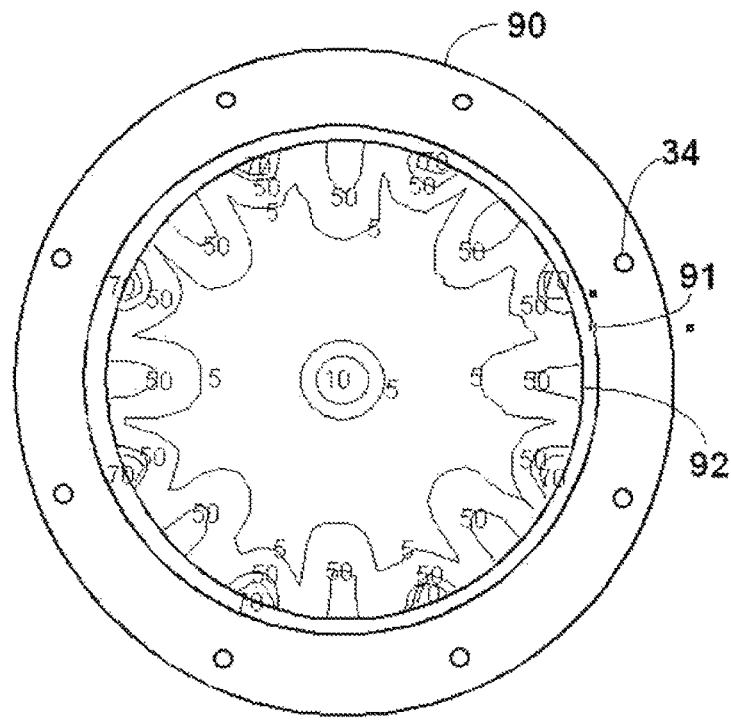
Figure 35:
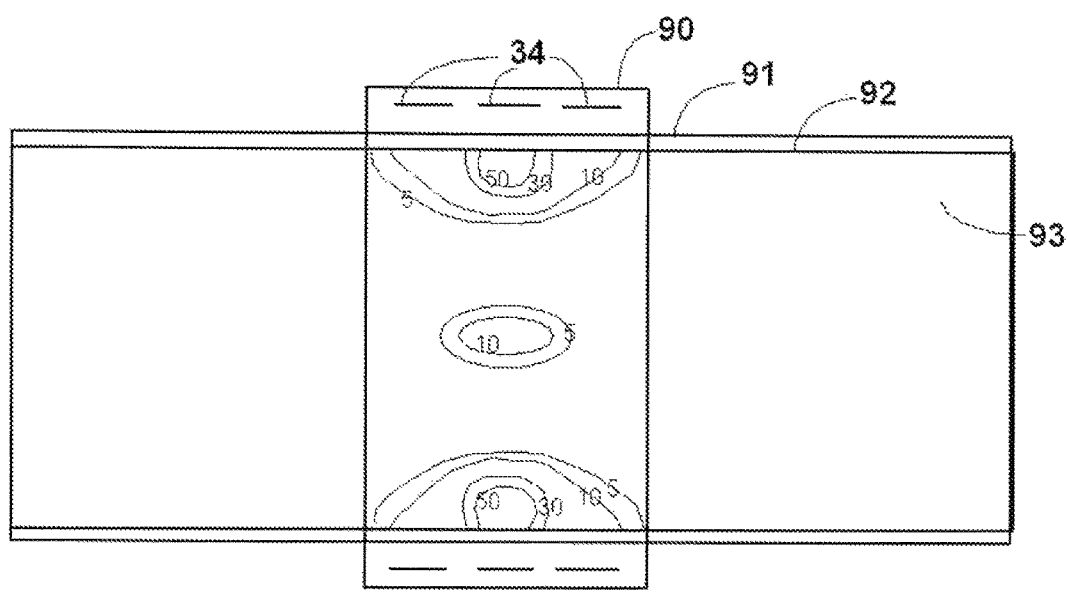

FIGS. 34 and 35 show the result of operation of the system used for generating FIGS. 30-33 but using a frequency of 434 MHz. As indicated above, the system has a circular cross section bolus with an outer diameter of 36 cm. and three antenna ring with the shorter antennas so the length of the bolus is 19 cm in the axial direction along the outside of and surrounding the tissue model 93 as shown in FIG. 35. The bolus liquid is deionized water. For the heating pattern of FIGS. 34 and 35, the system is operated as for FIGS. 30 and 31 to generate a central heating zone. However, for FIGS. 34 and 35, the operating frequency is 434 MHz rather than 250 MHz. FIGS. 34 and 35 show central SAR contours for 5% and 10% SAR, but this is not a useful heating zone. All heating zones are spaced around the tissue model fat tissue interface. This is a completely unsatisfactory heating pattern since no desired heating takes. The calculation for the A and C distances in the bolus as described for FIG. 6, and the phase difference calculated, shows a phase difference of 465 degrees. The criteria that such phase difference should not exceed 135 degrees is not met.

Figure 36:
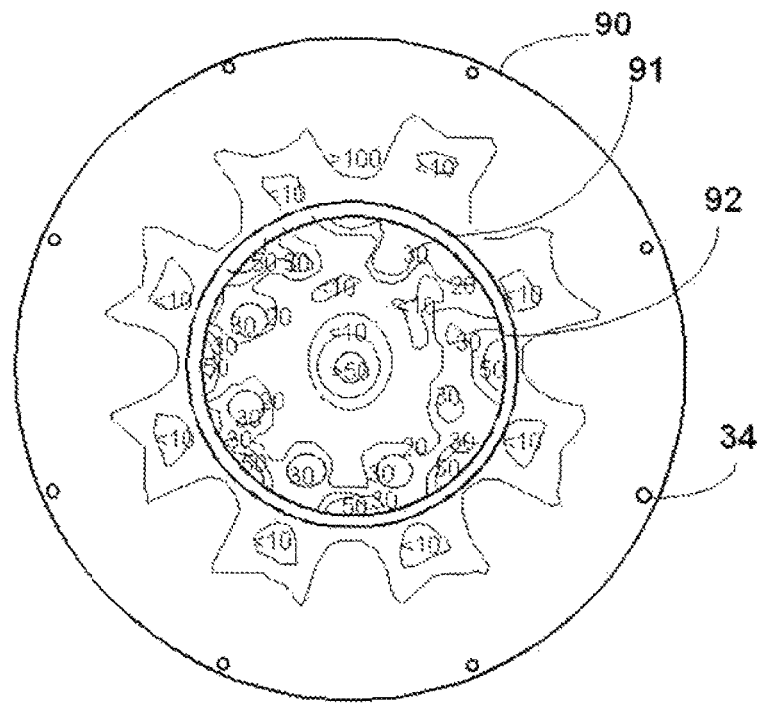
Figure 37:
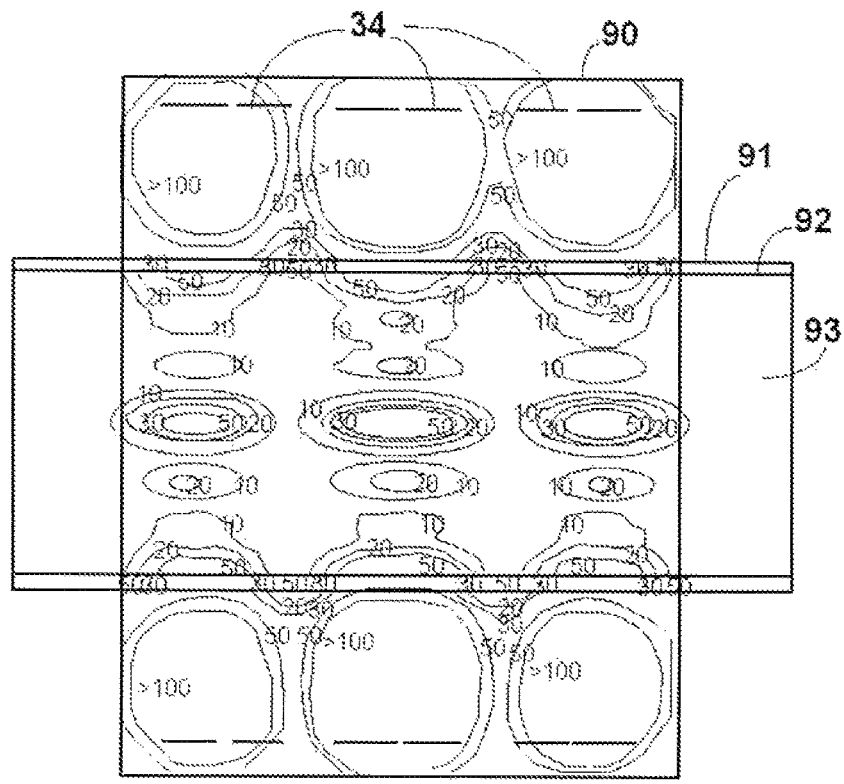

FIGS. 36 and 37 show the result of operation of a system similar to that of FIGS. 21 and 22 having a 60 cm outside circular diameter propylene glycol filled bolus and an antenna array of three rings of eight antennas each. The bolus extends for a length of 48 cm in the axial direction along the outside of and surrounding the tissue model 93. The tissue model is a circular cylindrical saline model. The difference in operation and the resulting heating patterns from those shown in FIGS. 21 and 22 is that the antenna array is operated at a frequency of 434 MHz as opposed to the 250 MHz which resulted in FIGS. 21 and 22. FIG. 36 is a horizontal section through the center of the tissue model and shows a substantially circular, small 50% SAR heating zone generated in the center of the tissue model. An area marked as <10 around the central heating zone indicates an area of substantially no heating. Hot spots occur around the circumference of the tissue inside and through the fat layer, and the outer portion of the propylene glycol bolus outwardly from the >100 SAR contour line and around the antennas is heated to a substantially greater extent than anywhere in the tissue. FIG. 37 shows the heating along the longitudinal axis of the tissue model and shows three separated longitudinally spaced center heating zones along the longitudinal axis. There is substantial non heating also within the tissue along the longitudinal axis between the separated heating zones. The hot spots around the circumference of the tissue inside and through the fat layer also occur in four separated areas along the longitudinal axis that appear as circumferential bands of fat heating. Also, the very hot >100 SAR area around the bolus and antennas shown in FIG. 36, is shown as occurring as three separate very hot ring areas spaced along the outside of the tissue surface aligned with the three rings of antennas and extending from the antennas inwardly toward, but not actually touching, the outer surface of the tissue model. This is a completely unsatisfactory heating result because the two outer central heating zones would be outside of the desired central heating zone so would heat normal tissue as would be the hot spots along the edge of the tissue model. Further, most of the power would be used heating the >100 SAR areas in the bolus and the propylene glycol bolus would require substantial cooling. This is because at the higher frequencies the propylene glycol is significantly higher in its dielectric losses.

An evaluation of the system arrangement generating the heating patterns of FIGS. 36 and 37 shows that at the high frequency of 434 MHz, the ratio of the distance between adjacent stacked antenna feed points along the longitudinal axis to the wavelength of the propylene glycol bolus, is greater than 0.8 and the spacing would result in a 3D focus phase difference of 200 degrees which is more than the 125 degrees found acceptable by the inventors.

Figure 38:
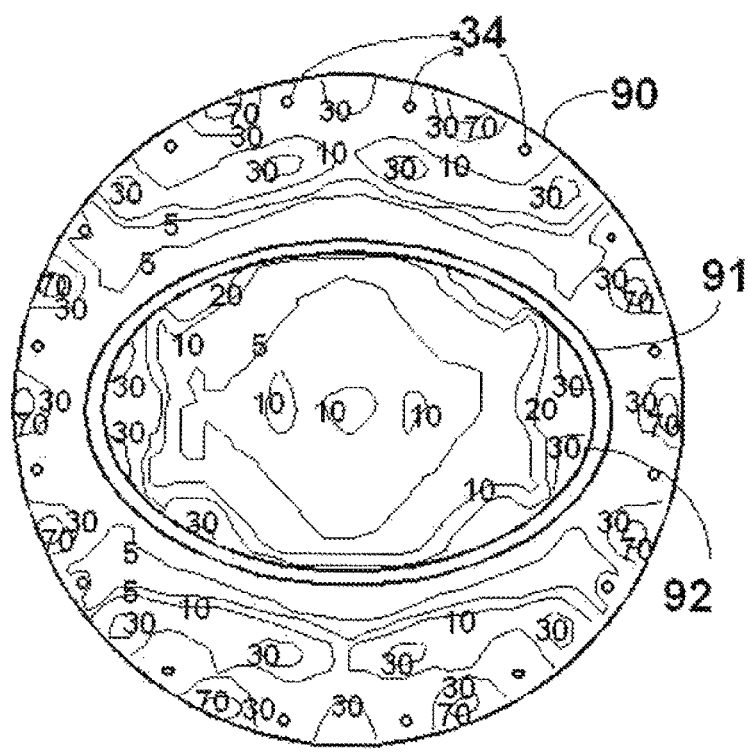
Figure 39:
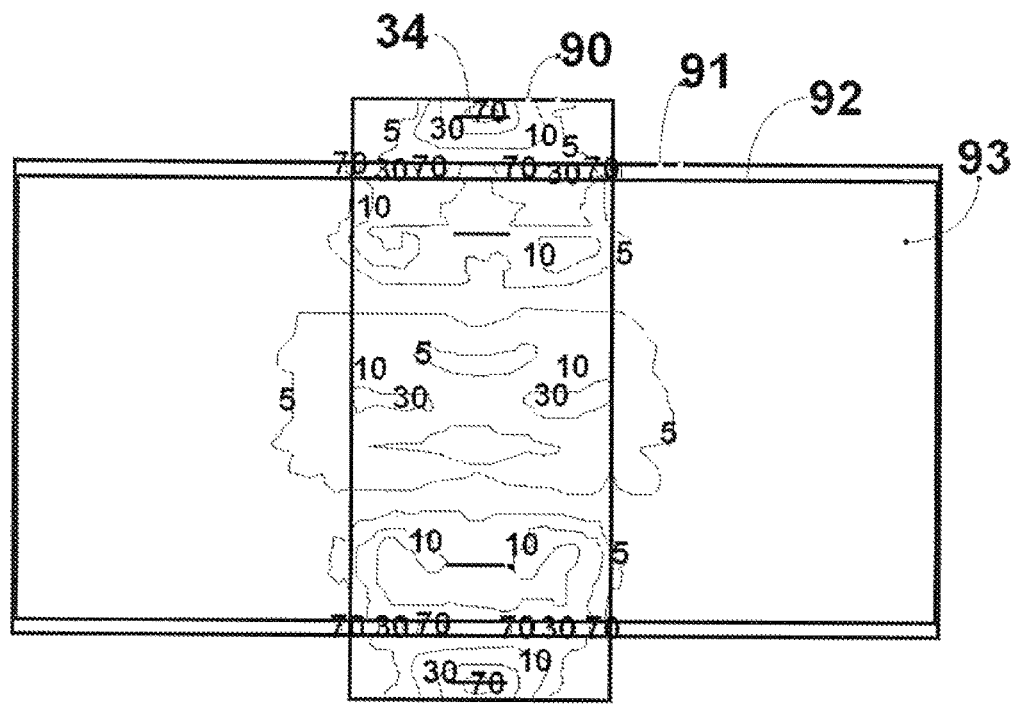

FIGS. 38 and 39 show the result of operation of a system having a single ring of sixteen antennas with a deionized water filled bolus having an outer diameter of 44 cm and extending for a length of 20 cm in the axial direction along the outside of and surrounding the tissue model 93 as shown in FIG. 39. The tissue model is an elliptical saline model having a major diameter of 35.5 cm and a minor diameter of 23 cm. FIG. 38 is a horizontal section through the center of the tissue model and shows that no areas of at least 50% SAR are created. Thus, there are no effective heating zones created in the tissue model. FIG. 39 shows hot spots in the fat tissue and both figs. show hot spots around the antennas. For this system at a frequency of 434 MHz the A dimension distance shown in FIG. 6 between antennas and the closest tissue surface varies from 6 cm to 11 cm. For A=8.4 cm the C-A phase is 400 degrees which exceeds the recommended 135 degrees value, and the results shown is poor central heating. The double hot zones in the center are a result of the poor selection of water bolus.

Figure 40:
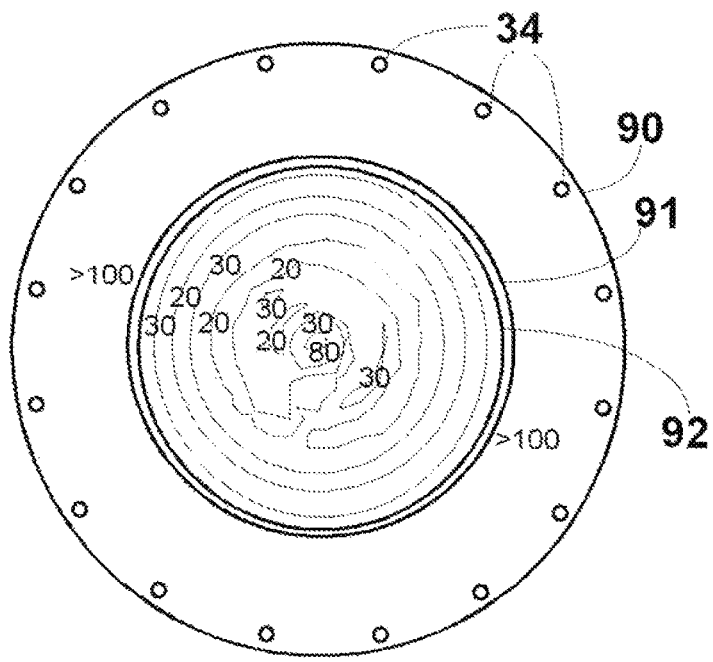
Figure 41:
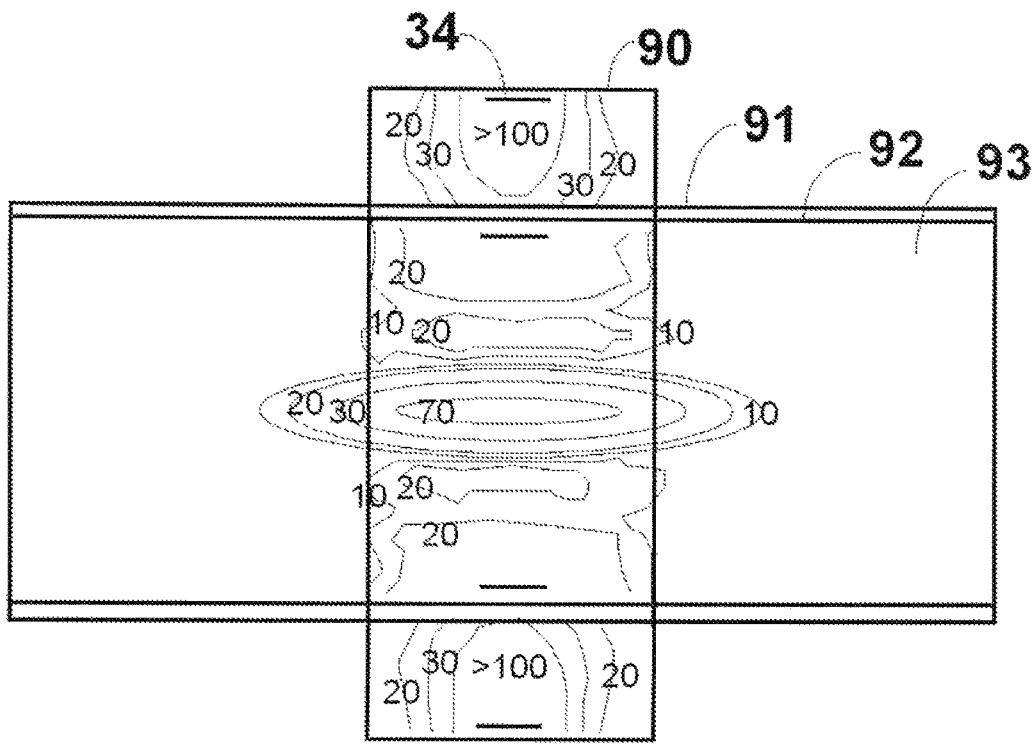

FIGS. 40 and 41 show the result of operation of a system having a single ring of sixteen antennas with a propylene glycol filled bolus having an outer diameter of 44 cm and extending for a length of 20 cm in the axial direction along the outside of and surrounding the tissue model 93 as shown in FIG. 41. The tissue model is a circular saline model having a diameter of 28 cm. FIG. 40 is a horizontal section through the center of the tissue model and shows a small heating zone within an 80% SAR contour that is within a larger zone within a 30% SAR contour. The heating zone has a volume of 89 cc. The entire bolus is shown having an SAR greater than 100%. Thus the bolus is very hot with only a very small central hot heating zone. In this example, the A value is 16.04 cm with propylene glycol having a dielectric of 26. The C-A phase would be 200 degrees if only an eight dipole antenna ring was used. However, the system used for FIGS. 40 and 41 has 16 dipole antennas in the ring leading to the C-A value actually being only 100 degrees. This would not then exceed the recommended 135 degree maximum. This shows there is a center focus, but two other dipole rings of 16 dipoles would be needed to provide convergent focusing along the long phantom axis which is not shown.

Figure 42:
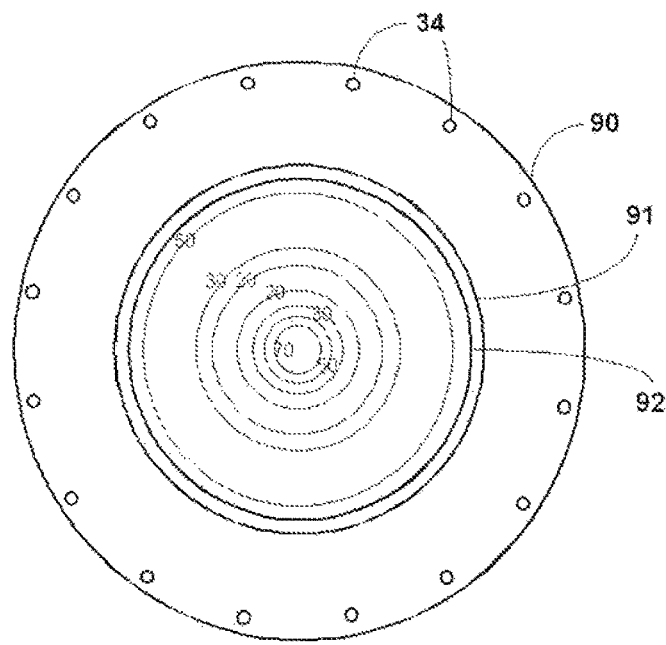
Figure 43:
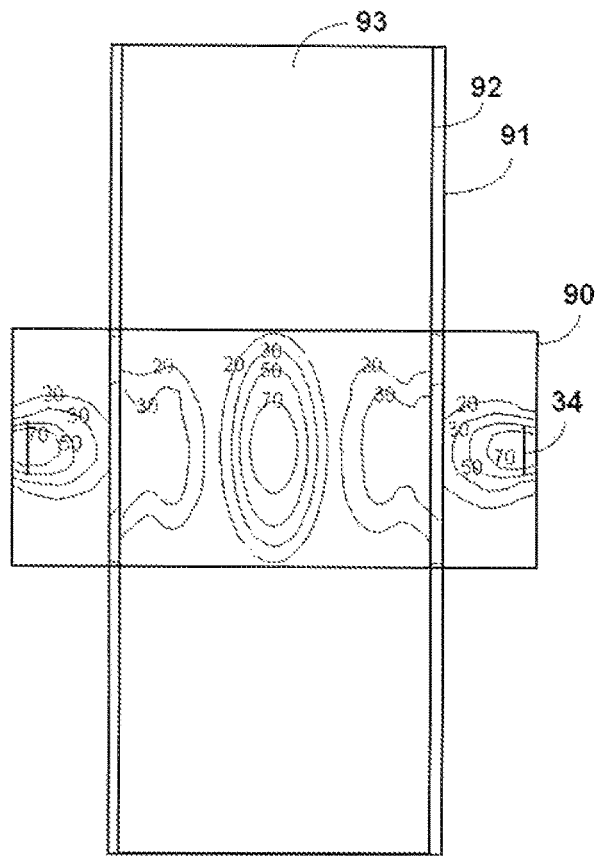

FIGS. 42 and 43 show the result of operation at a frequency of 250 MHz of a system having a single ring of sixteen antennas with a propylene glycol filled bolus having an outer diameter of 44 cm and extending for a length of 20 cm in the axial direction along the outside of and surrounding the tissue model 93 as shown in FIG. 43. The tissue model is a circular saline model having a diameter of 28 cm. FIG. 42 is a horizontal section through the center of the tissue model and shows a heating zone within a 50% SAR contour. The central heating zone has a volume of 89 cc. A ring of 50% SAR is shown just within the tissue-fat layer interface. About the entire outer half of the bolus has an SAR greater than 50% near the dipoles. In this example, the A value for the distance between the dipole and the tissue is 8.04 cm. If a 250 MHz frequency was used with the propylene glycol bolus having only eight antennas, the C-A phase variation would be 135 degrees, right at the recommended limit. In this case, there are 16 antennas along the propylene glycol bolus making the actual C-A difference for FIGS. 42 and 43 only 78 degrees. This system is then shown to be within the proper criteria for good central heating which is shown in the figures. This is only a single ring example and three rings would be needed to provide for further central convergence along the phantom long axis. However, this example also shows use of a narrower bolus width which can also provide some limitation to the long axis SAR pattern as shown in the next FIG. 43.

Figure 44:
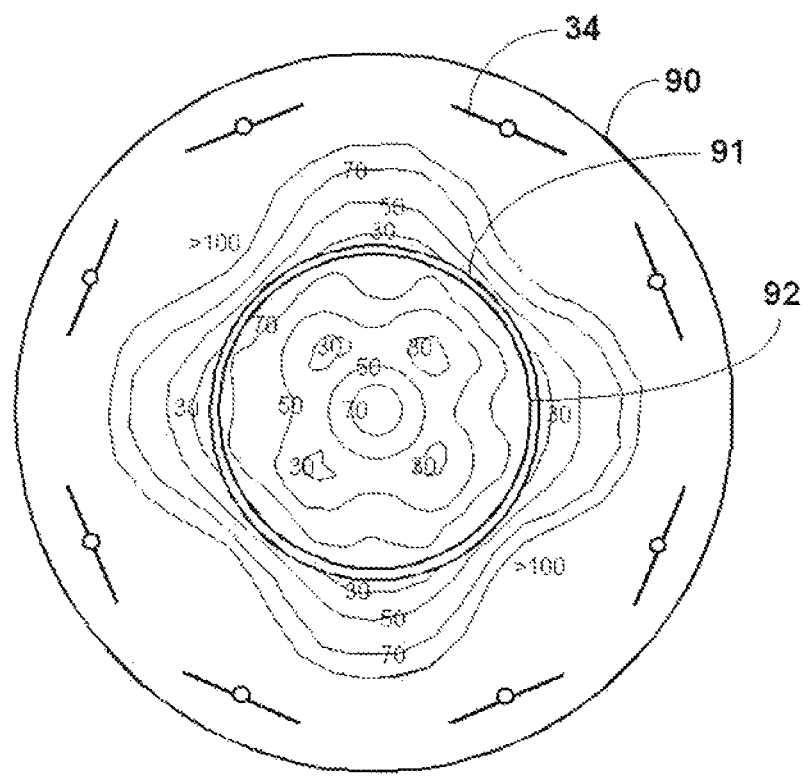
Figure 45:
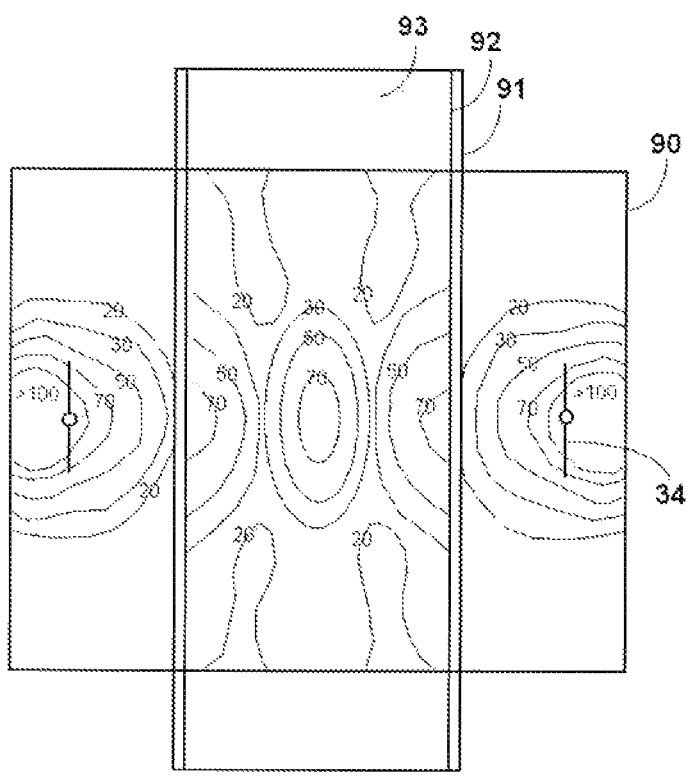

FIGS. 44 and 45 show the result of operation of a system having a single ring of eight orthogonal dipole antennas as shown in FIG. 11 with a propylene glycol filled bolus having an outer diameter of 60 cm and extending for a length of 48 cm in the axial direction along the outside of and surrounding the tissue model 62 as shown in FIG. 10. The system is operated at a frequency of 250 MHz. The tissue model is a circular saline model having a diameter of 28 cm. FIG. 44 is a horizontal section through the center of the tissue model and shows a heating zone within a 50% SAR contour. The central focused heating zone has a volume of 624 cc. Heating zones are shown along the tissue-fat layer interface and all of the bolus is shown with significant heating. This example uses an A value of 16.04 cm. This results in a C-A value of 115 degrees. This is within the 135 degree criteria for good central heating and steering. This figure also shows the use of the two orthogonal pairs of dipoles, each dipole being connected to a different RF power channel. In this case the dipoles are all operated with the same input phase. This will cause the polarization of the radiated electric field from the dipole pair to be tilted to a 45 degree angle relative the two orthogonal dipoles. This change in polarization makes changes to the heating pattern within the tissue as shown. Such a polarization at times may be preferred when a more horizontal electric field is needed to avoid cooler zones in the target tissues due to adjacent low dielectric structures such as large bone or fatty tissues that have interface surfaces that would have been nearly perpendicular to the non-tilted polarization.

Figure 46:
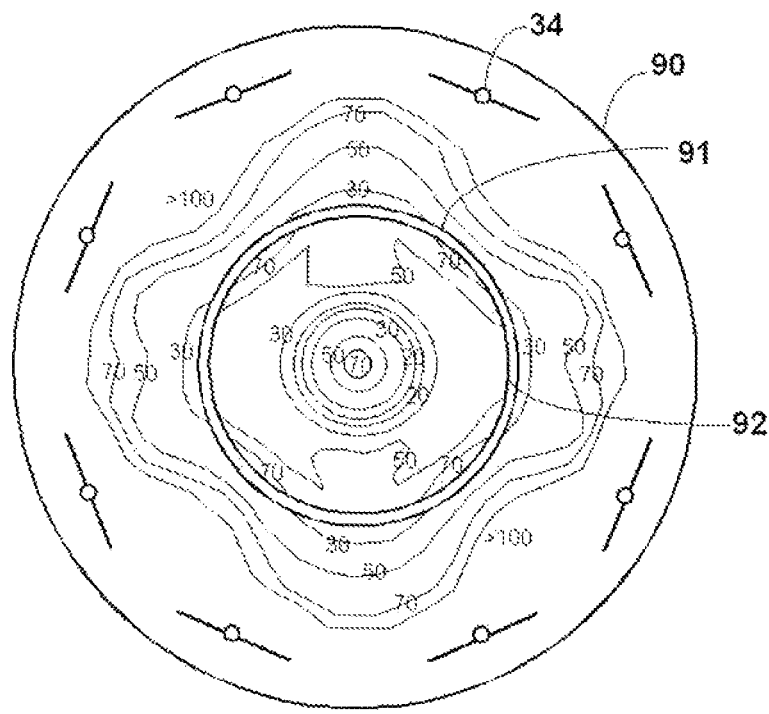
Figure 47:
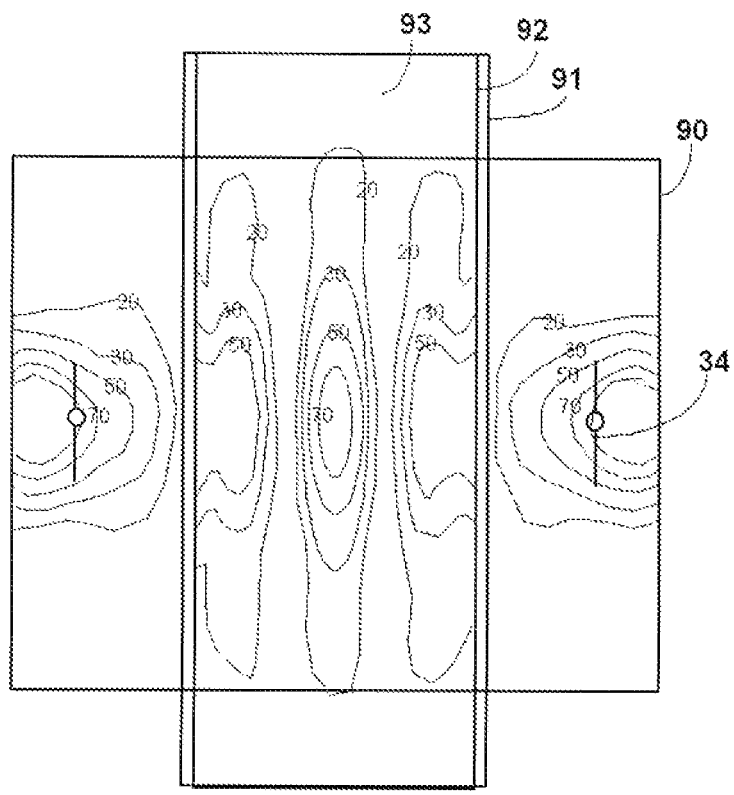

FIGS. 46 and 47 show the result of operation of a system having a single ring of eight orthogonal dipole antennas as shown in FIG. 11 with a propylene glycol filled bolus having an outer diameter of 60 cm and extending for a length of 48 cm in the axial direction along the outside of and surrounding the tissue model 62 as shown in FIG. 45. The system is operated at a frequency of 250 MHz. The tissue model is a circular saline model having a diameter of 28 cm. FIG. 46 is a horizontal section through the center of the tissue model and shows a central heating zone within a 50% SAR contour. The central heating zone has a volume of 236 cc. Four hot spot are shown along the tissue-fat layer interface and all of the propylene glycol bolus is shown with significant heating. As with FIGS. 44 and 45, this example uses an A value of 16.04 cm. This results in a C-A value of 115 degrees. This is within the 135 degree criteria for good central heating and steering. This figure also shows the use of the two orthogonal pair of dipoles, each dipole being connected to a difference RF power channel. For these figs., dipoles are set at 90 degree phase difference to make a circular polarized electric field. The dipole pairs that are on opposite sides have a 180 degree difference on the added dipoles so that the phase of these that arrive in the center will be adding as in-phase electrical vectors. FIG. 47 shows good central focus, but due to a single dipole ring has an elongated heating pattern along the long tissue axis. The addition of other antenna rings with phase focus could reduce the very long central heating length from that shown in FIG. 47.

Figure 48:
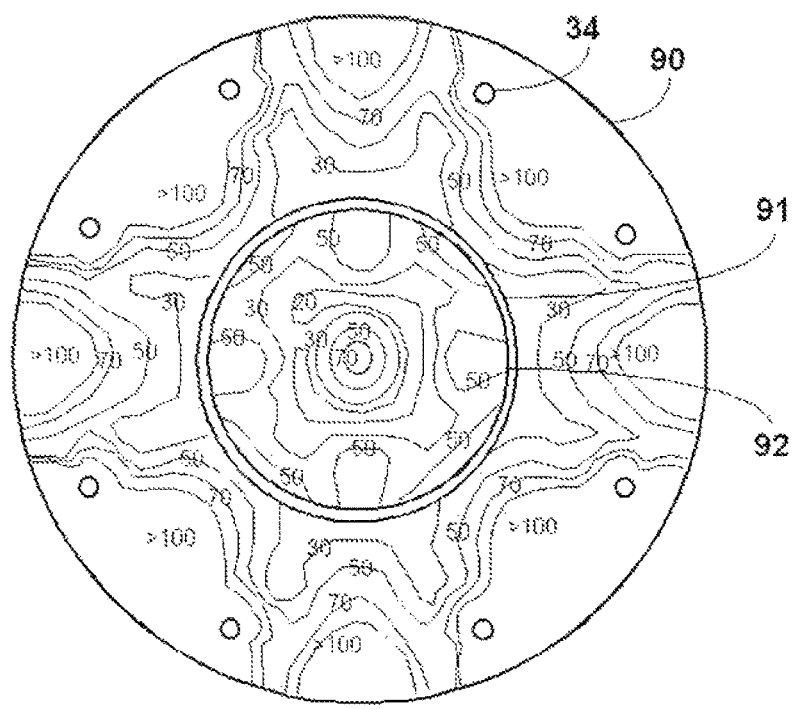
Figure 49:
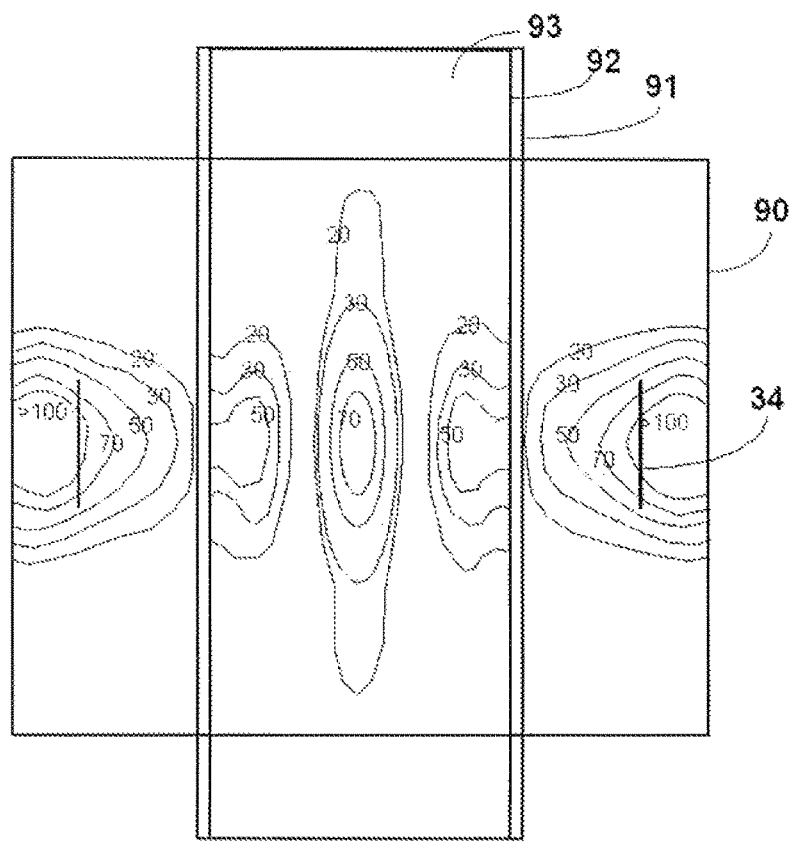

FIGS. 48 and 49 show the result of operation of the same system as used for FIGS. 46 and 47, but with only the dipoles of each orthogonal pair extending in the long Z axis being operated. Where only the dipoles extending in the long Z axis are operated, the fat layer SAR % is lower and the muscle SAR % along the muscle-fat layer interface surface is higher than FIGS. 46 and 47. The central heating zone has a volume of 199 cc. This operation is like the power was turned off on the newly added X axis dipoles of each orthogonal dipole pair. This shows how altering the power or phase to the dipoles or dipole orthogonal pairs can be use to provide useful changes in the SAR patterns in the tissue. FIG. 49 shows good central focus, but due to a single dipole ring has an elongated heating pattern along the long tissue axis. The addition of other antenna rings with phase focus could reduce the very long central heating length from that shown in FIG. 49.

Figure 50:
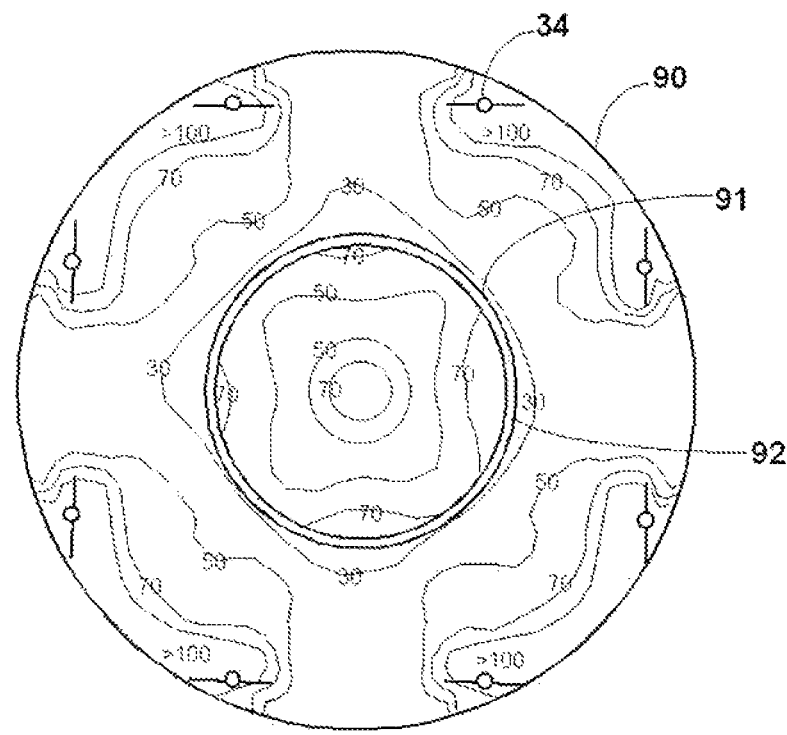
Figure 51:
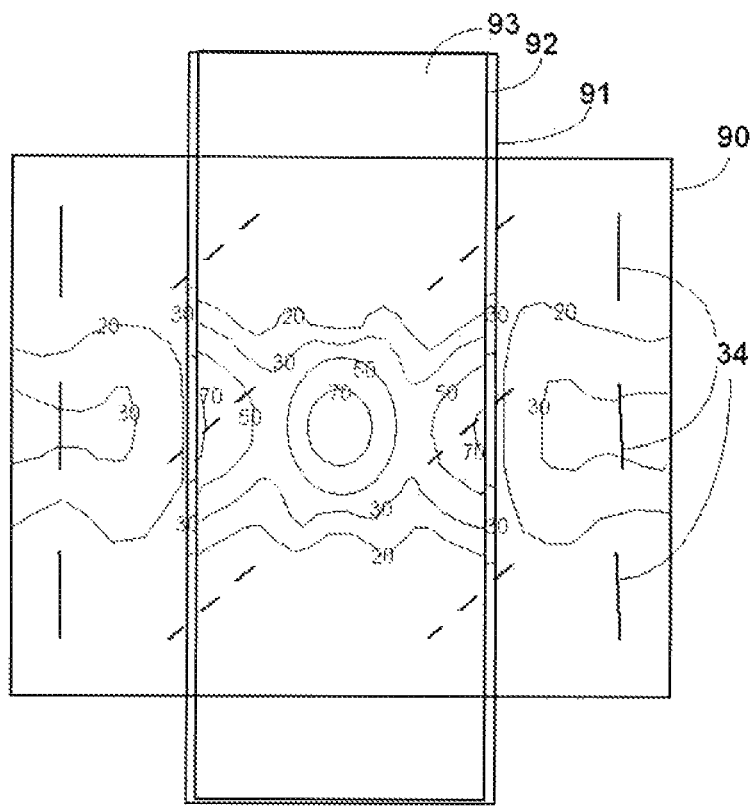

FIGS. 50 and 51 show the result of operation of a system having three rings of eight dipole antennas as shown in rotated of the Z axis with a 45 degree tilt angle relative to the longitudinal axis as shown in FIG. 51. The system has a propylene glycol filled bolus with an outer diameter of 60 cm and extending for a length of 48 cm in the axial direction along the outside of and surrounding the tissue model 93 as shown in FIG. 51. The tissue model is a circular saline model having a diameter of 28 cm. The system is operated at a frequency of 250 MHz. with a 75.6 degree phase lag for the applicators in the center ring. FIG. 50 is a horizontal section through the center of the tissue model and shows a central heating zone within a 50% SAR contour. The heating zone has a volume of 545 cc. Hot spot are shown along the tissue-fat layer interface and in the bolus between alternating pairs of antennas partially due to partially nonsymmetrical antenna placement. This system operation creates a good central focus zone because the phase variation of A-C is 115 degrees which is within the 135 degree recommended limit FIGS. 52-55 are tables containing results of various simulations using system parameters indicated and FIGS. 56-59 show various relevant properties.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A radio frequency annular phased array hyperthermia system to provide a heated focal zone in a selected position in a tissue mass, said hyperthermia system comprising:
    a bolus adapted to be positioned around the tissue mass in which the heated focal zone is to be provided to form an interface with the outer surface of the tissue mass, said bolus having a size and having a bolus media therein with a bolus media dielectric constant;
    a plurality of radio frequency energy radiator applicators positioned in at least one ring around the tissue mass in which the heated focal zone is to be provided and spaced by the bolus media a distance from the surface of the tissue mass to radiate radio frequency signals of a predetermined frequency through the bolus media into the tissue mass wherein the electric field of the radiated signals from each radio frequency energy radiator applicator are superimposed in a controlled manner to produce the heated focal zone in the selected position in the tissue mass, each radio frequency energy radiator applicator having a center and spaced substantially equally from respective adjacent radio frequency energy radiator applicators circumferentially around the at least one ring,
    wherein
    the radio frequency energy radiator applicators are spaced, the bolus is sized, and the bolus media dielectric constant is selected so that the distance between centers of respective adjacent radio frequency energy radiator applicators around the at least one ring is no greater than 0.8 of the wavelength of the radio frequency signal of the predetermined frequency in the bolus media and the difference in phase at a bolus-tissue mass interface point between a radiated signal traveling through the bolus between the center of a radio frequency energy radiator applicator and the center of the tissue mass and a signal traveling through the bolus to that point from the center of an adjacent radio frequency energy radiator applicator is no more than 135 degrees.

2. A radio frequency annular phased array hyperthermia system to provide a heated focal zone in a selected position in a tissue mass according to claim 1, and to provide 3D steering and focusing of the heated focal zone within the tissue mass, wherein the plurality of radio frequency energy radiator applicators are positioned in at least three rings around and spaced by the bolus media from the tissue mass with the at least three rings stacked along a longitudinal axis of the tissue mass to provide 3D steering and focusing of the heated focal zone within the tissue mass, wherein the at least three rings of radio frequency energy radiator applicators are spaced along the longitudinal axis of the tissue mass so that respective radio frequency energy radiator applicators in each ring are aligned and have a longitudinal separation distance between adjacent aligned radio frequency energy radiator applicators no greater than 0.8 of the wavelength of the radio frequency signal of the predetermined frequency in the bolus media and the difference in phase at the bolus-tissue mass interface between signals from the center of aligned stacked radio frequency energy radiator applicators mid way between the rings is no more than 125 degrees.

3. A radio frequency annular phased array hyperthermia system according to claim 2, wherein the predetermined frequency is greater than 150 MHz.

4. A radio frequency annular phased array hyperthermia system according to claim 3, wherein the predetermined frequency is between 150 MHz and 300 MHz.

5. A radio frequency annular phased array hyperthermia system to provide a heated focal zone in a selected position in a tissue mass according to claim 3, wherein the size of the bolus is determined by an outside diameter of the bolus and wherein the outside diameter of the bolus is between 36 cm and 60 cm.

6. A radio frequency annular phased array hyperthermia system to provide a heated focal zone in a selected position in a tissue mass according to claim 5, wherein the bolus media dielectric constant is between about 20 and 40.

7. A radio frequency annular phased array hyperthermia system according to claim 6, wherein the bolus media comprises alternating layers of materials in the bolus, such materials having different dielectric constants and arranged perpendicularly to the direction of the dominant electric field applied to the bolus.

8. A radio frequency annular phased array hyperthermia system to provide a heated focal zone in a selected position in a tissue mass according to claim 2, wherein the number of radio frequency energy radiator applicators in a ring is at least 8.

9. A radio frequency annular phased array hyperthermia system to provide a heated focal zone in a selected position in a tissue mass according to claim 2, wherein the total number of radio frequency energy radiator applicators in the phased array is at least 24.

10. A radio frequency annular phased array hyperthermia system to provide a heated focal zone in a selected position in a tissue mass according to claim 2, wherein the number of rings is three.

11. A radio frequency annular phased array hyperthermia system according to claim 2, wherein each of the plurality of radio frequency energy radiator applicators radiate a linearly polarized electric field that is aligned with the tissue mass longitudinal axis.

12. A radio frequency annular phased array hyperthermia system according to claim 2, wherein the plurality of radio frequency energy radiator applicators are dipole antennas.

13. A radio frequency annular phased array hyperthermia system according to claim 12, wherein a plurality of the plurality of radio frequency energy radiator applicators are arranged in pairs with one dipole antenna in each pair arranged orthogonally to the other dipole antenna in that pair, and wherein the power and phase of the radio frequency energy radiated by each antenna pair can be separately controlled wherein the radio frequency energy radiated by a dipole antenna pair can be linearly polarized at various selected angles or can be elliptically or circularly polarized.

14. A radio frequency annular phased array hyperthermia system according to claim 2, wherein the plurality of radio frequency energy radiator applicators are dipole antennas, and wherein a plurality of the plurality of radio frequency energy radiator applicators are arranged in pairs with one dipole antenna in each pair arranged orthogonally to the other dipole antenna in that pair, and wherein the power and phase of the radio frequency energy radiated by each antenna pair can be separately controlled wherein the radio frequency energy radiated by a dipole antenna pair can be linearly polarized at various selected angles or can be elliptically or circularly polarized.

15. A radio frequency annular phased array hyperthermia system according to claim 2, wherein the bolus media in the bolus comprises alternating layers of materials having different dielectric constants and arranged perpendicularly to the direction of the dominant electric field applied to the bolus.

16. A radio frequency annular phased array hyperthermia system according to claim 15, wherein the bolus comprises alternating layers of a first material having a dielectric constant and a second material having a higher dielectric constant, wherein an effective dielectric constant of the bolus media is between the dielectric constant of the first material and the second material.

17. A radio frequency annular phased array hyperthermia system according to claim 16, wherein the first material is chosen from the group of a plastic, a rubber, an air chamber, and combinations thereof, and the second material is deionized water.

18. A method of constructing and operating a radio frequency annular phased array hyperthermia system to provide a heated focal zone of a desired size in a selected position in a tissue mass, said hyperthermia system including a plurality of radio frequency energy radiator applicators positioned in at least one ring around and spaced by a bolus media from the tissue mass to radiate radio frequency signals of a predetermined frequency through the bolus media into said tissue mass in a manner wherein the electric field of the radiated signals from each radio frequency energy radiator applicator are superimposed in a controlled manner to produce the heated focal zone in the selected position in the tissue mass, the plurality of radio frequency energy radiator applicators having a specific number of radio frequency energy radiator applicators, each radio frequency energy radiator applicator having a center and the bolus media having a dielectric constant and an interface with the outer surface of the tissue mass, and the system having the plurality of radio frequency energy radiator applicators arranged in the at least one ring around the tissue mass to have an applicator separation distance between the centers of respective adjacent radio frequency energy radiator applicators in the at least one ring, an applicator spaced distance between the center of each radio frequency energy radiator applicator and a direct interface point located at the bolus-tissue mass intersection along the path from the center of a radio frequency energy radiator applicator to the center of the tissue mass, and a diagonal distance between the center of an adjacent radio frequency energy radiator applicator and a direct interface point, comprising the steps of:
   determining an operating frequency to provide a desired size of the heated focal zone in the tissue mass;
   determining the number of radio frequency energy radiator applicators in the plurality of radio frequency energy radiator applicators to be arranged around the tissue mass, the size of the bolus between the radio frequency energy radiator applicators and the tissue mass, and the bolus media dielectric constant so that at the determined frequency, the applicator separation distance is no greater than 0.8 of the wavelength of the radio frequency signal of the determined frequency in the bolus media and the difference in phase at the direct interface point between a radio frequency signal of the determined frequency traveling through the bolus media along the applicator spaced distance and the radio frequency signal of the determined frequency traveling along the diagonal distance is no more than 135 degrees.

19. A method of constructing and operating a radio frequency annular array hyperthermia system to provide a heated focal zone of a desired size in a selected position in a tissue mass, according to claim 18, wherein the plurality of radio frequency energy radiator applicators include radio frequency energy radiator applicators positioned in at least three rings around and spaced by the bolus media from the tissue mass and stacked along a longitudinal axis of the tissue mass to provide 3D focusing of the heated focal zone within the tissue mass, wherein the three rings of radio frequency energy radiator applicators being spaced along the longitudinal axis of the tissue mass so that respective radio frequency energy radiator applicator in each ring are aligned and have a longitudinal separation distance between adjacent aligned radio frequency energy radiator applicators, and with a 3D focus distance extending from the center of adjacent aligned radio frequency energy radiator applicators to a middle interface point at the bolus interface with the tissue mass surface midway between the adjacent radio frequency energy radiator applicators, comprising:

determining in coordination with the steps of claim 18, the number of radio frequency energy radiator applicators in the plurality of radio frequency energy radiator applicators to be arranged equally in each of the rings around the tissue mass, the size of the bolus between the antennas and the tissue mass, and the bolus media dielectric so that at the determined frequency, the applicator longitudinal separation distance is no greater than 0.8 of the wavelength of the radio frequency signal of the determined frequency in the bolus media and the difference in phase at the middle interface point between the radio frequency signals from longitudinally adjacent radio frequency energy radiator applicators is no more than 125 degrees.

* * * * *